(12) United States Patent
Martins et al.

(10) Patent No.: US 10,815,518 B2
(45) Date of Patent: Oct. 27, 2020

(54) SAMPLER AND METHOD OF PARAMETERIZING OF DIGITAL CIRCUITS AND OF NON-INVASIVE DETERMINATION OF THE CONCENTRATION OF SEVERAL BIOMARKERS SIMULTANEOUSLY AND IN REAL TIME

(71) Applicants: José António Martins, Itapira-SP (BR); Marcelo Adorni Pereira, Itapira-SP (BR); Vanderlei Pereira Ferreira, Mogi das Druzes-SP (BR)

(72) Inventors: José António Martins, Itapira-SP (BR); Marcelo Adorni Pereira, Itapira-SP (BR); Vanderlei Pereira Ferreira, Mogi das Druzes-SP (BR)

(73) Assignees: José António Martins, Itapira-SP (BR); Marcelo Adorni Pereira, Itapira-SP (BR); Vanderlei Pereira Ferreira, Mogi das Druzes-SP (BR)

( * ) Notice: Subject to any disclaimer, the term of this patent is extended or adjusted under 35 U.S.C. 154(b) by 664 days.

(21) Appl. No.: 15/668,129

(22) Filed: Aug. 3, 2017

(65) Prior Publication Data
US 2018/0037929 A1 Feb. 8, 2018

(30) Foreign Application Priority Data
Aug. 3, 2016 (PT) .......................... 109565

(51) Int. Cl.
*G01N 33/48* (2006.01)
*G01N 33/50* (2006.01)
*C12Q 1/6804* (2018.01)
*A61B 5/1455* (2006.01)
*A61B 5/145* (2006.01)
*C07K 14/47* (2006.01)
*C12Q 1/6841* (2018.01)
*C12Q 1/6876* (2018.01)
*G01N 23/04* (2018.01)
*G01N 33/58* (2006.01)

(52) U.S. Cl.
CPC .......... *C12Q 1/6804* (2013.01); *A61B 5/1455* (2013.01); *A61B 5/14546* (2013.01); *C07K 14/47* (2013.01); *C12Q 1/6841* (2013.01); *C12Q 1/6876* (2013.01); *G01N 23/04* (2013.01); *G01N 33/587* (2013.01); *G01N 33/588* (2013.01); *A61B 2560/0425* (2013.01); *A61B 2562/146* (2013.01)

(58) Field of Classification Search
None
See application file for complete search history.

*Primary Examiner* — Russell S Negin
(74) *Attorney, Agent, or Firm* — Leason Ellis LLP

(57) ABSTRACT

A sampler and a method of parameterization by calibration of digital circuits and non-invasive determination of the concentration of several biomarkers simultaneously and in real time. The method makes use of equipment which, from a set of luminous signatures—spectrum—provided by a spectrophotometer (E5) (E6), applies a digital filter that breaks down the spectrum into sub-spectra that shows the digital signatures of relevant markers and, through a digital decoder, the concentration of a set of several biomarkers is obtained simultaneously and in real time.

20 Claims, 14 Drawing Sheets

Platelets

Platelets (without grouping [μ])

Platelets

Platelets (without sampler)

Platelet

MCHC

Erythrocyte

Hemoglobin

Hematocrit

MCV

Leucocyte

MCH

| Individual | S – biomarkers – n=8 | | | | | | | | Pathologies – j=5 | | | | |
|---|---|---|---|---|---|---|---|---|---|---|---|---|---|
| ID | Erythrocyte | Hemoglobin | Hematocrit | MCV | MCH | MCHC | Platelets | Leucocyte | Dengue | Hypertension | Hepatitis | Diabetes | Cardiovascular |
| 1 | 4.4 | 13.4 | 4.1 | 91.14 | 30.45 | 33.42 | 181,000 | 6,200 | 0 | 1 | 0 | 1 | 1 |
| 2 | 4.43 | 13.9 | 41.2 | 93 | 31.38 | 33.74 | 195,000 | 4,300 | 0 | 1 | 1 | 1 | 1 |
| 3 | 4.6 | 14.2 | 41.4 | 90 | 30.87 | 34.3 | 204,000 | 4,100 | 0 | 1 | 0 | 1 | 0 |
| 6 | 4.53 | 13.8 | 40.1 | 88.52 | 34.6 | 34.41 | 303,000 | 10,100 | 0 | 0 | 1 | 0 | 0 |
| 7 | 3.9 | 13.2 | 38.2 | 97.95 | 33.85 | 34.55 | 186,000 | 8,500 | 0 | 0 | 1 | 0 | 0 |
| ⋮ | ⋮ | ⋮ | ⋮ | ⋮ | ⋮ | ⋮ | ⋮ | ⋮ | ⋮ | ⋮ | ⋮ | ⋮ | ⋮ |
| 74 | 4.38 | 13.3 | 39.6 | 90.41 | 30.37 | 33.59 | 139,000 | 3,800 | 1 | 0 | 0 | 0 | 1 |
| 75 | 3.68 | 12.2 | 36.4 | 98.91 | 33.15 | 33.52 | 137,000 | 1,800 | 1 | 0 | 0 | 0 | 1 |
| 76 | 3.75 | 11.7 | 34.2 | 91.2 | 31.2 | 34.21 | 200,000 | 7,500 | 0 | 0 | 1 | 0 | 1 |
| 77 | 4.88 | 15.3 | 45 | 92.21 | 31.35 | 34 | 196,000 | 8,100 | 0 | 0 | 1 | 0 | 0 |
| 78 | 4.37 | 14 | 41.3 | 94.51 | 32.04 | 33.94 | 241,000 | 6,400 | 0 | 1 | 0 | 0 | 0 |
| 79 | 4.01 | 11 | 32.7 | 81.55 | 27.43 | 33.64 | 197,000 | 4,200 | 0 | 1 | 0 | 1 | 0 |
| 80 | 4.16 | 12.5 | 36.5 | 87.74 | 30.05 | 34.25 | 245,000 | 4,800 | 0 | 0 | 0 | 1 | 0 |
| ⋮ | ⋮ | ⋮ | ⋮ | ⋮ | ⋮ | ⋮ | ⋮ | ⋮ | ⋮ | ⋮ | ⋮ | ⋮ | ⋮ |
| 220 | 4.11 | 12.2 | 36.2 | 88.08 | 29.68 | 33.7 | 288,000 | 5,400 | 0 | 1 | 0 | 1 | 0 |

FIG. 11

| $P_n$ | Algorithm | $P_n$ | Algorithm | $P_n$ | Algorithm |
|---|---|---|---|---|---|
| $P_1$ | Mean Centering (MC) | $P_{10}$ | Derivatisation Direct Orthogonalization (DO) | $P_{19}$ | Partial Least Squares (PLS) |
| $P_2$ | Centroid Centering (CC) | $P_{11}$ | Neuro-Genetic Network | $P_{20}$ | Partial Least Squares Discriminatory Analysis (PLS-DA) |
| $P_3$ | Normalization - Standard Normal Variate (SNV) | $P_{12}$ | Savitzky-Golay derivation | $P_{21}$ | Neural Network |
| $P_4$ | Probabilistic Quotient Normalization (PQN) | $P_{13}$ | Norris-Williams derivation | $P_{22}$ | Partial Least Squares (PLS) and Fuzzy Numbers |
| $P_5$ | Orthogonal Signal Correction (OSC) | $P_{14}$ | Extended Multiplicative Signal Correction (EMSC) | $P_{23}$ | Evolutionary Algorithms and its Neuro-Fuzzy-Genetic combinations |
| $P_6$ | Multiplicative Scatter Correction (MSC) | $P_{15}$ | Extended Inverted Signal correction (EISC) | $P_{24}$ | Regression by Classical Least Squares |
| $P_7$ | Savitsky-Golay (Sav-gol) | $P_{16}$ | Optical Path Length Estimation and Correction (OPLEC) | $P_{25}$ | Regression Supported by Vector machines |
| $P_8$ | Log Decay Scaling (Log-DS) | $P_{17}$ | Kaiser HoloReact (KHR) | $P_{26}$ | Principal Component Regression (PCR) |
| $P_9$ | Variance Scaling (VS) | $P_{18}$ | Haar Transform (HT) | $P_{27}$ | Mean Centering and Fuzzy Numbers |

FIG. 12

| Spectrum | Erythrocyte $[\overline{z^1}]$ | Hemoglobin $[\overline{z^2}]$ | Hematocrit $[\overline{z^3}]$ | MCV $[\overline{z^4}]$ | MCH $[\overline{z^5}]$ | MCHC $[\overline{z^6}]$ | Platelets $[\overline{z^7}]$ | Leucocytes $[\overline{z^8}]$ |
|---|---|---|---|---|---|---|---|---|
| 1 | -0.085988 | 0.023331 | -0.161754 | 0.195064 | 0.054967 | -0.053248 | -0.029368 | 0.001154 |
| 2 | -0.085676 | 0.018602 | -0.168304 | 0.187679 | 0.047816 | -0.050607 | -0.031250 | 0.005442 |
| 3 | -0.086028 | 0.013282 | -0.175114 | 0.182199 | 0.041386 | -0.049135 | -0.033356 | 0.010381 |
| 3 | -0.086341 | 0.009890 | -0.181320 | 0.178662 | 0.037448 | -0.046808 | -0.033797 | 0.009211 |
| 5 | -0.085031 | 0.012366 | -0.181207 | 0.175141 | 0.038016 | -0.043240 | -0.026587 | -0.005305 |
| 6 | -0.081757 | 0.018067 | -0.175218 | 0.167189 | 0.040596 | -0.039215 | -0.015066 | -0.025344 |
| 7 | -0.077020 | 0.022703 | -0.167386 | 0.153341 | 0.042279 | -0.035443 | -0.004546 | -0.042819 |
| 8 | -0.071387 | 0.026760 | -0.157311 | 0.137683 | 0.043624 | -0.032023 | 0.002050 | -0.054899 |
| 9 | -0.048542 | 0.047447 | -0.112912 | 0.083156 | 0.051444 | -0.013626 | 0.029624 | -0.116973 |
| ⋮ | ⋮ | ⋮ | ⋮ | ⋮ | ⋮ | ⋮ | ⋮ | ⋮ |
| 70 | -0.011951 | -0.043506 | 0.032412 | -0.038284 | 0.036076 | -0.054351 | 0.152491 | -0.074237 |
| 71 | -0.078166 | -0.057186 | 0.041913 | -0.101219 | 0.087283 | -0.052909 | 0.172594 | -0.001378 |
| ⋮ | ⋮ | ⋮ | ⋮ | ⋮ | ⋮ | ⋮ | ⋮ | ⋮ |
| 125 | 0.001302 | 0.001909 | -0.015939 | 0.007751 | -0.018772 | 0.005372 | 0.008223 | 0.118342 |

FIG. 13A

| Spectrum | Erythrocyte $[\overline{z^1}]$ | Hemoglobin $[\overline{z^2}]$ | Hematocrit $[\overline{z^3}]$ | MCV $[\overline{z^4}]$ | MCH $[\overline{z^5}]$ | MCHC $[\overline{z^6}]$ | Platelets $[\overline{z^7}]$ | Leucocytes $[\overline{z^8}]$ |
|---|---|---|---|---|---|---|---|---|
| 1 | 0.050626 | -0.329141 | 0.494147 | -0.313826 | 0.071689 | -0.130755 | 0.178777 | -0.237593 |
| 2 | 0.040675 | -0.318079 | 0.388059 | -0.256823 | 0.053604 | -0.079991 | 0.104978 | -0.140588 |
| 3 | 0.032816 | -0.301777 | 0.296298 | -0.206791 | 0.041660 | -0.040673 | 0.047971 | -0.062214 |
| 3 | 0.026929 | -0.281544 | 0.217145 | -0.164229 | 0.033921 | -0.008943 | 0.003613 | 0.003130 |
| 5 | 0.023078 | -0.258110 | 0.150842 | -0.130060 | 0.029988 | 0.015116 | -0.028661 | 0.055685 |
| 6 | 0.021236 | -0.231843 | 0.098205 | -0.104232 | 0.029835 | 0.030970 | -0.048802 | 0.094689 |
| 7 | 0.021270 | -0.203055 | 0.059462 | -0.085972 | 0.033084 | 0.038645 | -0.057896 | 0.120734 |
| 8 | 0.022959 | -0.172488 | 0.033681 | -0.074436 | 0.038810 | 0.039032 | -0.058087 | 0.136000 |
| 9 | 0.024511 | -0.142951 | 0.008575 | -0.062442 | 0.043058 | 0.040192 | -0.061104 | 0.153466 |
| ⋮ | ⋮ | ⋮ | ⋮ | ⋮ | ⋮ | ⋮ | ⋮ | ⋮ |
| 70 | -0.094090 | -0.025041 | 0.044073 | 0.159810 | -0.168670 | -0.043600 | 0.042749 | 0.032575 |
| 71 | -0.115550 | -0.007108 | 0.045754 | 0.144854 | -0.159370 | -0.070470 | 0.046208 | 0.037164 |
| ⋮ | ⋮ | ⋮ | ⋮ | ⋮ | ⋮ | ⋮ | ⋮ | ⋮ |
| 125 | 0.049124 | 0.057562 | 0.095669 | 0.052286 | 0.017708 | -0.095080 | -0.036060 | -0.043810 |

FIG. 13B

| Standard | Max Error % | Standard | Max Error % | Standard | Max Error % | Standard | Max Error % |
|---|---|---|---|---|---|---|---|
| 99.00% | 3.62 | 60.00% | 2.17 | 20.00% | 1.12 | 5.00% | 5.16 |
| 80.00% | 3.71 | 40.00% | 1.05 | 10.00% | 2.16 | 2.00% | 8.11 |

FIG. 14

| Biomarkers | Samples [S] necessary | $P_n$ | Iterations |
|---|---|---|---|
| Erythrocytes | 220 | 1,2,3,22,19 | 145 |
| Hemoglobin | 220 | 3,4,5,6,20 | 100 |
| Hematocrit | 220 | 1,2,3,4,6,7,26 | 150 |
| MCV | 220 | 4,5,6,7,27 | 160 |
| MCH | 220 | 6,7,8,9,22,19 | 145 |
| MCHC | 220 | 17,3,4,5,8,22,19 | 124 |
| Platelets | 220 | 18,3,2,5,6,22,19 | 135 |
| Leucocytes | 220 | 15,16,18,1,2,3,25 | 130 |
| Myeloblast | 220 | 27,4,1,2,3,4,5,25 | 120 |
| Myelocyte | 220 | 5,6,7,8,14,15,25 | 80 |
| Metamyelocyte | 220 | 14,13,15,5,4,3,25 | 90 |
| Banded Neutrophil | 220 | 27,3,2,1,18,22,19 | 95 |
| Segmented Neutrophil | 220 | 27,1,2,3,22,19 | 85 |
| Eosinophil | 220 | 27,3,4,5,6,22,19 | 75 |
| Lymphocyte | 220 | 27,1,2,3,4,6,7,24 | 150 |
| Basophil | 220 | 26,4,5,6,7,24 | 165 |
| Monocyte | 220 | 27,6,7,8,9,24 | 180 |
| LDL cholesterol | 200 | 27,17,3,4,5,8,24 | 200 |
| VLDL cholesterol | 200 | 27,18,3,2,5,6,25 | 220 |
| Coagulation | 200 | 15,16,18,1,2,3,24 | 280 |
| Vitamin 25-OH D | 200 | 27,4,1,2,3,4,5,24 | 290 |
| Dihydrotestosterone | 200 | 27,5,6,7,8,14,15,24 | 255 |
| Total Creatine kinase | 200 | 27,14,13,15,5,4,3,26 | 260 |
| Total Cholesterol | 250 | 27,15,16,18,1,2,3,25 | 160 |
| HDL Cholesterol | 250 | 27,4,1,2,3,4,5,25 | 140 |
| Reactive Protein C | 230 | 27,5,6,7,8,14,15,25 | 120 |
| Glutamic Oxaloacetic Transaminase - GOT | 240 | 27,3,2,1,18,22,19,25 | 155 |
| Glutamate-pyruvate Transaminase - GPT | 240 | 27,1,2,3,25 | 144 |
| Sodium | 300 | 3,4,5,6,25 | 185 |
| Potassium | 300 | 1,2,3,4,6,7,25 | 80 |
| Coagulation | 250 | 27,4,5,6,7,22,19 | 90 |
| Total Creatine kinase | 220 | 27,6,7,8,9,22,19 | 98 |
| Cardiac isoform of Creatine kinase | 220 | 27,17,3,4,5,8,22,19 | 94 |
| Total Troponin | 220 | 18,3,2,5,6,22,19 | 96 |
| Glycose | 240 | 15,16,18,1,2,3,22,19 | 105 |

FIG. 15

| Biomarkers | Samples [S] necessary | $P_n$ | Iterations |
|---|---|---|---|
| Gamma-GT | 300 | 278,4,1,2,3,4,5,26 | 110 |
| Amylase | 260 | 5,6,7,8,14,15,24 | 115 |
| Promonocyte | 300 | 14,13,15,5,4,3,23 | 118 |
| Prolymphocyte | 300 | 27,3,2,1,18,22,19,26 | 120 |
| Plasmocytes | 350 | 28,1,2,3,25 | 122 |
| NS1 - Quick Dengue Test | 150 | 3,4,5,6,27 | 124 |
| Creatinine | 200 | 27,1,2,3,4,6,7,24 | 150 |
| Creatine Phosphokinase SE (Total CK) | 200 | 27,4,5,6,7,26 | 168 |
| Creatine Phosphokinase SE (MB Fraction) | 200 | 2,6,7,8,9,24 | 175 |
| Cardiac Troponin I | 250 | 17,3,4,5,8,2 | 180 |
| Triglycerides | 250 | 18,3,2,5,6,22,19 | 140 |
| Homocysteine | 200 | 2,3,2,1,18,19,26 | 246 |
| Complete blood count - HT | 200 | 1,2,3,27 | 100 |
| Reactive Protein C | 200 | 3,4,5,6,26 | 200 |
| Phosphorus | 300 | 1,2,3,4,6,7,22,19 | 150 |
| Urea | 300 | 4,5,6,7,25 | 170 |
| Beta HCG | 350 | 6,7,8,9,25 | 165 |
| CPK - Creatine kinase | 250 | 17,3,4,5,8,25 | 178 |
| CPK-MB - Creatine kinase - MB | 250 | 18,3,2,5,6,25 | 175 |
| Serology for Toxoplasmosis - Antibody class IgM | 350 | 17,3,4,5,8,23 | 240 |
| Serology for Toxoplasmosis - Antibody class IgG | 350 | 6,7,8,9,23 | 245 |
| Creatine Phosphokinase | 250 | 15,16,18,1,2,3,22,19 | 160 |
| Group Systems | 300 | 27,4,1,2,3,4,5,20 | 164 |
| Triiodothyronine T3 | 350 | 5,6,7,8,14,15,21 | 155 |
| Free Thyroxine T4 | 350 | 14,13,15,5,4,3,21 | 200 |
| Thyroid-stimulating Hormone | 350 | 3,2,1,18,22,19,24 | 220 |
| VDRL | 300 | 27,1,2,3,24 | 230 |
| Surface Anti-Antigen of Hepatitis B | 350 | 3,4,5,6,24 | 250 |
| Surface Antigen of Hepatitis B | 350 | 27,1,2,3,4,6,7,24 | 256 |
| Antibody of Hepatitis C antivirus | 300 | 27,4,5,6,7,24 | 245 |

FIG. 15 (CONT.)

SAMPLER AND METHOD OF PARAMETERIZING OF DIGITAL CIRCUITS AND OF NON-INVASIVE DETERMINATION OF THE CONCENTRATION OF SEVERAL BIOMARKERS SIMULTANEOUSLY AND IN REAL TIME

FIELD OF THE INVENTION

The present invention relates to a sampler and a method of parameterization by calibration digital circuits and non-invasive determination of the concentration of several biomarkers simultaneously and in real time.

BACKGROUND OF THE INVENTION

The technologies and solutions available in the market nowadays are, most of the time, restricted to the determination of glucose concentration, with special incidence in the monitoring of diabetes (type I and II). Even though it is considered to be a noteworthy advance, due to the great necessity to monitor diseases associated with diabetes and the possibility of developing and implementing advanced therapies as well, it is still insufficient since these technologies and solutions need to cover other types of pathologies in only one step.

Recently (2016), Furukawa Hiromitsu disclosed a spectrophotometer, which operates in the wavelength interval from 500 to 1700 nm (near infra-red), and uses an optical set based in "Multichannel Fourier-transform (McFT)". This spectrophotometer is capable of detecting fat directly from blood vessels in real time. The spectra are obtained with a white light source that passes through the tissues of the human finger, and are collected by an optical fiber cable which leads them to a McFT optical set that filters and breaks down the light into two offset waves which are captured by an electronic sensor. The electronic sensor composes a spectrum in real time where the peak at 1200 nm corresponds to the concentration or fat in blood. The author refers that the process depends on the blood volume at the tip of the finger and on the calibration made in vitro with the help of another bench-top spectrophotometer. This equipment cannot be portable because:

its optical set is sensible to movements;
  it uses transmittance as sampling that requires high potency of light to overcome the tissues of the finger;
  due to the optical set used, the set of values used to calibrate an equipment might not be replicable;
  there is no guarantee that the sample did not suffer variability, either because of patient movement or because of the susceptibility to movement of the optical system;
  shows the results of a single biomarker.

Document U.S. Pat. No. 9,277,880 (B2) relates to non-invasive methods, equipment and systems to obtain measurements of several components or analytes present in blood, such as glycose. It uses LED light and super luminescent LED light, as light source, which emits light in wavelengths between 1600 nm and 1700 nm. The detector comprises an array of diodes (photodetectors) that are geometrically distributed. The invention refers to the measurement of total haemoglobin, even though it mentions that the measurement of glycose is also possible. Therefore, this equipment is of single response, or for a few biomarkers. Even though it is potent, the light source emits in a restricted, spectral interval, therefore it is able to penetrate the tissues in the finger. However, measuring systems with restricted spectral emission intervals increase the imprecision of the results obtained. This document mentions "physiological parameter"—a general term for biomarker—the term biomarker is not mentioned unless it is the specific ones, glycose and total haemoglobin—even though it is monitoring the health state of the patient. The patent mentions the Lambert-Beer law, which implies that the system reads the concentration of biomarkers from absorption and not from reflectance. The document focuses on two biomarkers—total haemoglobin and glycose—and does not have the capacity to analyse other biomarkers. The results are not obtained from reflectance and it is not clear if the correlation is made by the Lambert-Beer law or by another way of correlation.

Document WO2015006160 (A2) discloses methods for the identifications of metabolic signatures, which are unique for autism, in blood plasma. The samples are analysed using several chromatographic techniques based on mass spectrometry to orthogonally measure a wide range of small metabolites with different molecular weights found in samples from patients with autism and compared to control samples from individuals without autism. These individual metabolites, or group of metabolites, function as autism indicators. Those metabolic signatures are used in diagnostic methods to identify autistic individuals with precision. This document refers to an invasive analysis that is not made in real time and does not simultaneously show a set of biomarkers. Several chromatographic techniques with more than one kind equipment are also used, not as an option but as a necessity. On the other hand, the invention proposed in the present document uses only one kind of instrumentation in a specific spectral interval, between 400 nm and 2500 nm.

Document U.S. Pat. No. 8,946,389 (B2) discloses compositions and methods to identify or quantify one or more analytes in samples. The composition can comprise one affinity molecule reversibly conjugated with a portion of an identifier (tag) by means of a binding double stranded nucleic acid, or through an adapter molecule. The affinity molecule and the portion of the tag can be linked to different chains of the double stranded nucleic acid ligand. The compositions can be used in any biologic assay to detect, identify and/or quantify target molecules or analytes, including multiplex staining for molecular profiles of individual cells or populations of cells. For example, the compositions can be adapted to be used in immunofluorescence, fluorescence in situ hybridization, immunohistochemistry, western blot and other similar techniques. This invention focuses directly in samples obtained with invasive methods and manipulates these samples with chemical agents. It is not a real time technique, with simultaneous results, and can also be contaminating since it depends on chemical agents.

The patent WO 2014121177 (A1) discloses biomarkers, methods, assays and kits that sire provided to predict the efficacy of adjuvant chemotherapy in an individual with lung cancer of non-small early stage cells. In contrast to the invention proposed in this document, the document WO 2014121177 (A1) is directed towards cancer diagnosis through chemical kits, which means it is not a technique that simultaneously presents several biomarkers without the necessity of obtaining and manipulating samples.

Document US 20120004854 (A1) discloses metabolic panels of blood serum biomarkers and methods for their use in the detection and diagnosis of cancer, especially ovarian cancer. The metabolic biomarker panels include several metabolites. Methods of supervised classification, such as "Machines Supported by Vectors", are used to determine if the levels of metabolic biomarkers in an individual are indicative for the presence of cancer. The biomarkers and methods described allow performing a cancer diagnosis with a precision, specificity and/or a sensibility of at least 80%. This is another example of a technique with a specific objective, directed towards ovarian cancer, which is also performed with the manipulation of blood samples, specifically blood plasma, which can be contaminating. The diagnosis needs more than the determination of a set of biomarkers, and they only support the diagnosis made by a medical professional.

U.S. Pat. No. 6,512,937 (B2) discloses methods that use multilayer techniques to estimate analytes in tissues extracted from the human body, which makes this technique invasive. This patent describes techniques that use several statistical analysis to classify spectral profiles and construct calibration models for the determination of biomarkers with clinical interest.

U.S. Pat. No. 7,050,847 (B2) describes non-invasive methods of analysis applied in the surveillance of biologic parameters directly in the human body fluid by means of measuring the skin impedance.

Patent US2015/0112170 (A1) describes a method used to do measurements, in a non-invasive way, to determine physiologic parameters, with the aim to track diabetes (type I and II), using terahertz radiation which crosses biologic tissue in vivo.

Document EP2337866 (B1) refers to in vivo methods to determine the probability of an individual to suffer from major depression. This probability is investigated through hypermapping based on the combination of mathematical parameters. The biomarkers analysed are related to the inflammatory, metabolic and neurotrophic biomarkers group. The method to determine the probability of an individual to suffer from major depression, consists in the comparison between the vectors in the hyper map of a certain individual before and after the therapy.

Sakudo et al. have demonstrated in their last published works how non-invasive methods and specific analytic systems, associated with several statistical analysis of data, can be used as useful tools to provide complementary diagnosis information, in order to help the health professional diagnosing chronic fatigue syndrome.

The methods available in the market nowadays perform the concentration determination of only one biomarker at a time, and do not consider the general health state of the individual, which usually interferes in the determination of relevant biomarkers related to the health state of the individual.

With the material presented, and the research done in the scientific literature, as well as in patients' data bases, there was no analytic method or device found to be capable of performing non-invasive analysis, that do not require blood samples, and shows both the results in real time and the concentration of n biomarkers simultaneously.

SUMMARY OF THE INVENTION

The invention disclosed in this document makes use of an equipment that applies a digital filter to a set of luminous signatures—spectrum—provided by a spectrophotometer. The digital filter breaks down the spectrum in sub-spectra which show the digital signatures of relevant markers and, through a digital decoder, the concentration of a set of several biomarkers is obtained simultaneously and in real time.

The method for parametering and determining the concentration can be considered to have two steps:

The first step known as calibration and validation, consists of the construction, calibration and validation of a filter and a decoder of luminous signatures from living tissue biomarkers. The reference standard for the calibration and validation of the digital filter-decoder pair is the concentration of n biomarkers from m different samples obtained from conventional and invasive methods, and the record of pathologies or health conditions of the m individuals that were the providers of these same samples. The digital filter breaks down the raw spectrum and the digital decoder obtains the concentration of n biomarkers, for the appropriate comparisons and validations.

The second step, known as the determination step or work routine, filters and decodes the reflectance detected by the spectrophotometer integrated in the equipment, to obtain the concentration values of n biomarkers simultaneously and in real time, without handling blood samples, without being invasive, without resorting to chemical or biological agents, and without producing pollutant residues.

This determination step is performed by a spectrophotometer-computer set, which can be easily transported and installed in any place with access to electrical power provided by any electrical source. The system is intuitive and comprises three steps:

patient identification;

placing the finger of the patient in the sampler to collect the spectra;

simultaneous and real time presentation of the concentration of n biomarkers.

To avoid a variability problem, which, for example, might occur due to the blood flow or patient movement during the spectra collection, the equipment referred to in the present invention collects about 15 spectra (samples) per second which corresponds to an instantaneous of blood components, and that by itself would be sufficient to minimize sample variability (the living tissue).

Since the normal spectra (samples) collection time is about 60 seconds, it is equivalent to say that approximately a thousand spectra (samples) are collected. The average obtained is valid if the standard deviation is less than 0.001, a precision that annuls a possible problem with variability and makes the result reliable.

The main advantage of the present invention is that the calibration and the validation ensures that the method of the present invention can replace conventional clinical analysis tests, as it ensures their accuracy and reliability. This reliability is guaranteed by the validation performed from several mathematical techniques that are measured and calibrated from conventional standard clinical analysis samples. The result of these measurements and calibrations constitute a numerical set or parameters that are coded and implemented in digital electronic circuits. These circuits, after being parameterized, filter the raw spectrum and decode it into biomarkers concentration values by presenting them in the conventional clinical analysis format, all in real time and simultaneously.

Another advantage of the present invention is to permit the operation of an equipment that, in the work routine, does not require blood sample manipulation, is non-invasive, non-contaminant, does not generate chemical or biological residues, and shows the concentration of several biomarkers simultaneously and in real time.

This invention permits the operational optimization of entities that perform analysis which allows obtaining the concentration of biomarkers present in blood, commonly known as "blood analysis". The main targets are emergency services and services that provide medical care, as well as clinical analysis laboratories and other health units.

Health clinics, where routine consultations are made, can also benefit from this invention. By using this invention, the patient can do the analysis in the clinic, where the health professional has access to the results of the analysis in the same consultation.

Obtaining the concentration of a set of n biomarkers simultaneously and in real time, in less than 5 minutes, makes it possible for the decisions and medical diagnosis to be performed faster. It allows optimizing the treatment and operational conditions of the health service, which in turn benefits the patient.

To the doctor or health professional, the fundamental difference between the results obtained in a non-invasive way by the equipment used in this invention and the results from conventional invasive methods, is only the speed with which the information is provided.

It has the potential to universalize clinical analysis, and be used in remote regions without laboratorial infrastructures, war zones, zones with natural disasters, etc.

Since it is non-invasive, this invention is not a contamination vector, and it contributes in an effective way to reduce hospital infections and even to prevent disease transmission.

It is comfortable, because it allows the user to obtain the concentration of n biomarkers without using needles or any other kind of device that provokes cuts, that causes pain or psychological implications. Therefore the present invention is not only advantageous for the common population, but is specially indicated for children, old people, people afraid of needles, and those who have sensitive blood vessels.

It is ecological, because it does not produce any type of chemical or biologic residue directly.

The determination step that applies the digital filter-decoder pair is performed in a spectrophotometer-computer set which can be transported easily and installed in any place with electric energy.

In the work routine the system operation is intuitive, since it only comprises three steps:
  patient identification;
  placing the finger of the patient in the sampler to collect the spectra;
  simultaneous presentation of the result of the concentration of a set of biomarkers in real time.

The concentration results of the biomarkers can be shown by print on paper or in a digital application installed in any type of computer equipment, namely smartphones, personal computers, etc., any equipment that can be provided with an application and that has a screen or an output peripheral, which allows its presentation.

The spectrophotometer used in the equipment where the sampler and the parametrized digital circuits of the present invention are implemented, is a portable spectrophotometer in the wavelength between 400 and 2500 nm, without optical components that are susceptible to movement, which is an indispensable condition to obtain the correct results. Any type of movement in the optical components, during transportation or during the collection, can risk the correct collection of samples.

The whole process of calibration and validation, created in the first step of this invention, is transferred to the second step. The data base obtained in the first step, with a single spectrophotometer, is used by other spectrophotometers used in the work routine.

In both steps of this invention, a possible sample variability, mainly because it is living tissue, is annulled, because the invention is structured to collect an average of 1000 spectra (samples) in less than 60 seconds. After calculating the average and standard deviation, the spectra average is accepted as a valid sample if the standard deviation is less than 0.001.

The way in which the invention is structured in the first step, which is the calibration and validation step, allows the substitution, the adaptation or the combination of mathematical algorithms referred to in the scientific literature, especially in chemometrics, or other new ones that might be introduced, in order to construct the filter that breaks down the raw spectra and to construct the decoder that obtains the set of biomarkers simultaneously. In the determination step, the digital circuits that filter and decode the spectra do not need to use any mathematical techniques or algorithms, since the determination of the concentration of the biomarkers is carried out based on the parameters constructed in the calibration step.

For this step, the calibration and validation step, the analytic systems found in the scientific literature and data bases of patent documents, do not take into consideration the crossing of the pattern organization of standard references with the health conditions of the individuals. Organizing the data by factors that are directly correlated with the health state of the individuals contributes to a better construction of this invention with a high index of correlation and precision.

BRIEF DESCRIPTION OF DRAWINGS

FIG. 11 shows an example of the $^1[S]_m^{n}$ $^1[\mu]_m^{j}$ data set.

FIG. 12 refers to examples of mathematical operators applied in the calibration step.

FIG. 13A shows an example of the first plane of the hypercube $\overline{[Z]}$ with eight biomarkers, after 120 iterations and validated.

FIG. 13B shows an example of the sixth plane of the hypercube $\overline{[Z]}$ with eight biomarkers, after 120 iterations and validated.

FIG. 14 shows the difference between spectrophotometers gauged by traceable standards of 2% to 99%.

FIG. 15 shows some of the biomarkers which concentrations can be obtained from the equipment and the method of this invention, showing the average quantity of [S] samples needed for calibration, the order and the algorithms used and referred to in FIG. 12, and the average quantity of iterations until validation.

DETAILED DESCRIPTION OF THE INVENTION

By shapes: "substantially ellipsoidal", "substantially convex", "substantially centered", "substantially parallel", refers to the preferential shapes to make the invention, even though the invention can function with other shapes as well.

The invention disclosed in this document is comprised of a sampler and a method of parameterizing digital circuits and non-invasively determining the concentration of several biomarkers simultaneously and in real time, implemented in an equipment.

Figure 9:
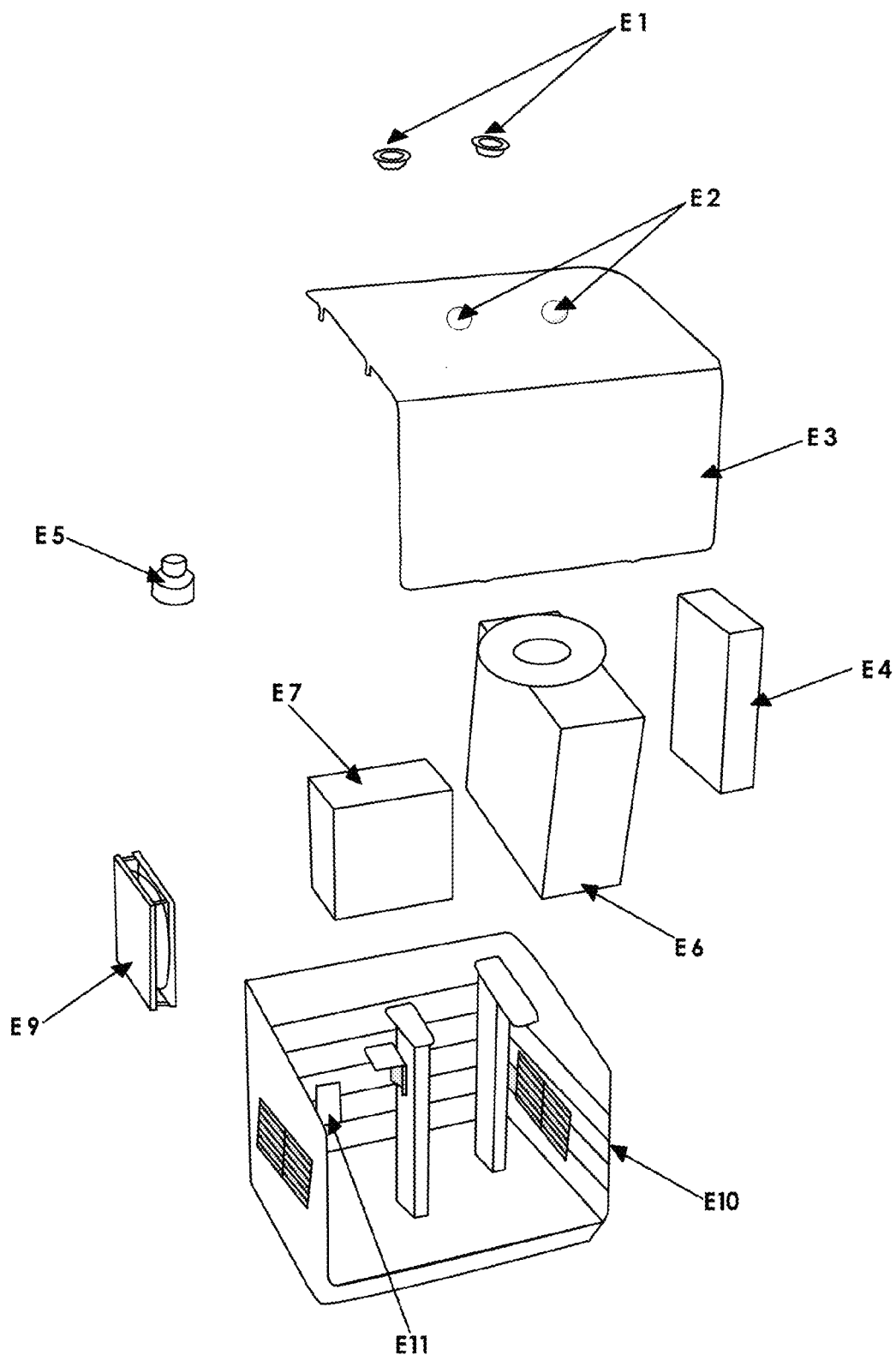
FIG. 9 shows the equipment where the sampler and the calibrated digital circuits of the present invention are implemented, used in the calibration and validation step, comprised by:
- E1—Sampler
- E2—Docking window of the sampler
- E3—Equipment lid
- E4—Energy source
- E5—Spectrophotometer 1
- E6—Spectrophotometer 2
- E7—Processing central unit
- E9—Forced refrigeration
- E10—Box
- E11—Power supply and data connector
Figure 10:
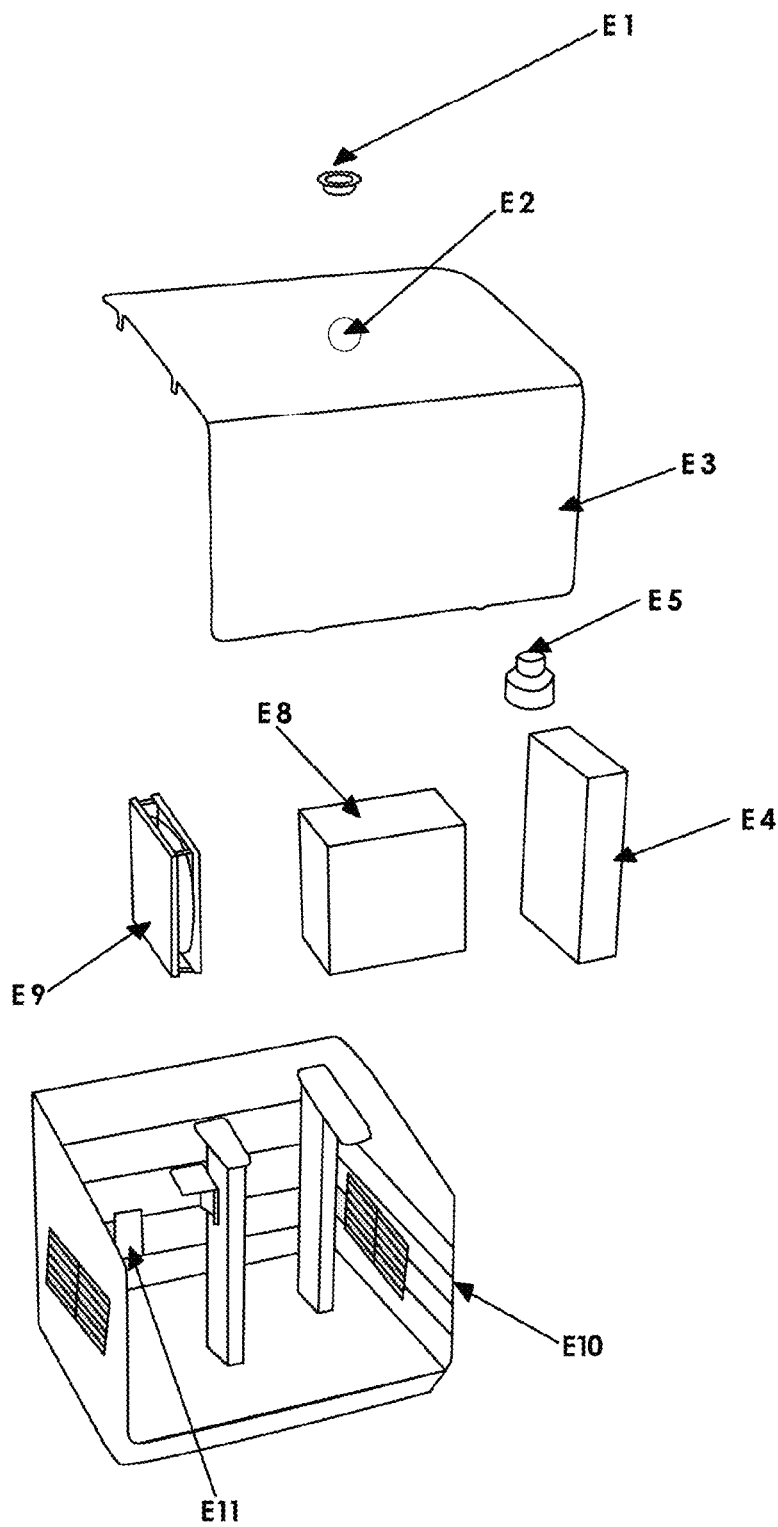
FIG. 10 shows the equipment used in the determination step, comprised by:
- E1—Sampler
- E2—Docking window of the sampler
- E3—Equipment lid
- E4—Energy source
- E5—Spectrophotometer
- E8—Processing central unit with the dedicated digital circuits N∥ and $\overline{[Z]}$
- E9—Forced refrigeration
- E10—Box
- E11—Power supply and data connector

In the calibration and validation step, as shown in FIG. 9, the equipment is comprised by:
- E1—Sampler
- E2—Docking window of the sampler
- E3—Equipment lid
- E4—Energy source
- E5—Spectrophotometer 1
- E6—Spectrophotometer 2
- E7—Processing central unit
- E9—Forced refrigeration
- E10—Box
- E11—Power supply and data connector In the determination step, as shown in FIG. 10, the equipment is comprised by:
- E1—Sampler
- E2—Docking window of the sampler
- E3—Equipment lid
- E4—Energy source
- E5—Spectrophotometer
- E8—Processing central unit with the dedicated digital circuits N∥ and $\overline{[Z]}$
- E9—Forced refrigeration
- E10—Box
- E11—Power supply and data connector Since the equipment used in the calibration and validation step is substantially identical to the one used in the determination step, as a matter of confidence in the data obtained in the first step the equipment has two samplers (E1) and two spectrophotometers (E5) (E6), and in the second step the equipment has one sampler (E1) and one spectrophotometer (E5).

Figure 8:
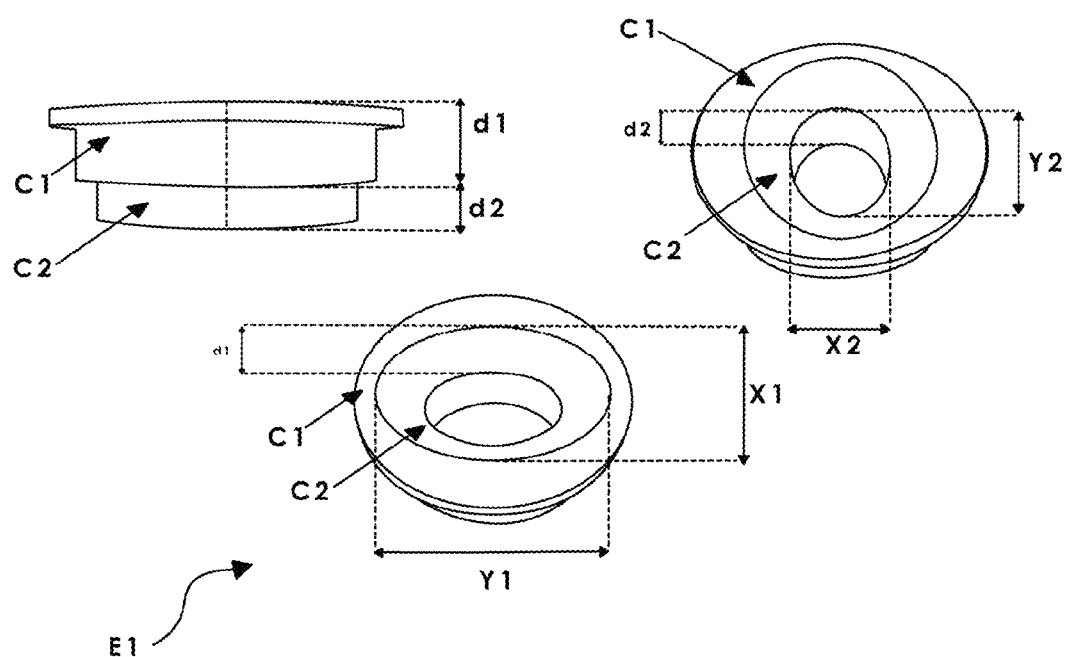
FIG. 8 shows several views of the sampler (E1) from the invention equipment where the finger of the patient is placed to collect the digital signatures by the spectrophotometer.

Sampler (E1) as represented in FIG. 8 is formed by two substantially ellipsoidal shapes (c1) (c2). The substantially ellipsoidal shapes have axis of different sizes, and are substantially centered, substantially parallel to each other. The substantially ellipsoidal shape (c1) presents:

- an $x_1$ axis with length between 0.01 mm and 40 mm, particularly between 10 mm and 30 mm, more specifically between 18 and 20 mm
- an $y_1$ axis with length between 0.01 mm and 45 mm, particularly between 10 mm and 35 mm, more specifically between 23 mm and 26 mm
- an height $d_1$ between 0.01 mm and 18 mm, particularly between 1 mm and 13 mm, more specifically between 3 mm and 8 mm;

it is found immediately above the substantially ellipsoidal form (c2) which presents:

- an $x_2$ axis with length between 0.01 mm and 31 mm, particularly between 5 mm and 21 mm, more specifically between 9 mm and 11 mm
- an $y_2$ axis with length between 0.01 mm and 36 mm, particularly between 10 mm and 26 mm, more specifically between 14 mm and 16 mm
- a height $d_2$ between 0.01 mm and 29 mm, particularly between 1 mm and 19 mm, more specifically between 2 mm and 9 mm.

The inferior surface of the substantially ellipsoidal shape (c1) shows a substantially convex shape that unites the superior edge of the substantially ellipsoidal shape (c1) and the edge of the substantially ellipsoidal shape (c2).

The shape of the sampler is essential to obtain correct results. The height $d_2$ of the substantially ellipsoidal shape (c2) prevents the finger of the patient from touching the spectrophotometer, as the substantially convex shape that unites the superior edge of the substantially ellipsoidal shape (c1) and the superior edge of the substantially ellipsoidal shape (c2), allows the correct accommodation of the finger.

The material in which this sampler is made has to obey technical characteristics that allow the measurement to be correctly made over time. The material has to be highly reflective, chemically and physically inert, and non-toxic to the patient. These characteristics need to be maintained over an extended period of time and allow several measurements to be made. One material that meets all these characteristics is, including but not limited to, polytetrafluorethylene (PTFE).

To obtain a set of human biomarkers, in a non-invasive way, simultaneously and in real time, the method described in this invention presents the following characteristics:

1. Is performed in two steps:

$1^{st}$ The calibration and validation step is an iterative process to create parameters to be implemented in a digital filter-decoder pair N‖-[Z] calibrated and validated from a known standard reference $^1[S]_m{}^n$. Contrary to the second step (determination step), the calibration step is not in real time. In this step, after the spectral data and the invasive samples have been collected, to each biomarker algorithms are chosen, adapted and combined in order to obtain the calibrated and validated parameters algorithm to be used in the determination step. Since the equipment does not use spectrophotometers with mobile optical components that are susceptible to variability, the transfer of the data obtained in the calibration step can be performed from a unique data base. All the calibration and validation of the system is performed from a single data base, always created in the first step (calibration and validation step) and transferred to the determination step. FIG. 14 shows the difference between spectrophotometers gauged by traceable standards from 2% to 99%, showing that the variability between these equipment is negligible. FIG. 15 presents some of the biomarkers, which concentrations can be obtained with the equipment and methods in this invention, referring to the order and the algorithms used that are referred to in FIG. 12, the quantity of samples needed to obtain the convergence and the correspondent quantity of iterations.

$2^{nd}$ Determination step or work routine, in real time, receives the raw spectrum, submits it to the digital filters N‖ e [Z] (parameterized in the calibration and validation phase) and obtains the concentration of several biomarkers simultaneously and in a non-invasive way.

Figure 6A:
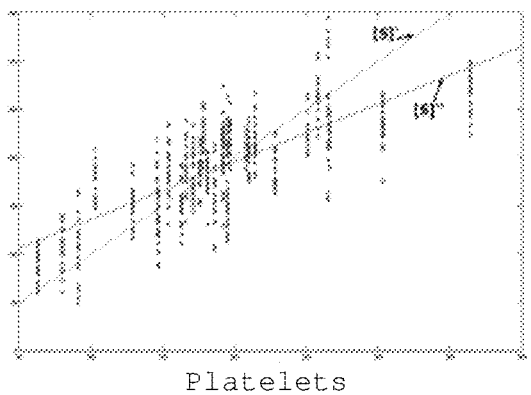
FIGS. 6A and 6B show how significant is the sampler of the invention, showing the result of the biomarker $[S^{platelet}]$ in 100 iterations with the samples obtained by the sampler of the invention, and the same kind of result but with samples collected without the sampler. Even after 300 iterations, the result cannot be accepted as valid. The axis in these figures refer to the standard obtained from an invasive method [S] against [SR]' and [SR]".
Figure 6B:
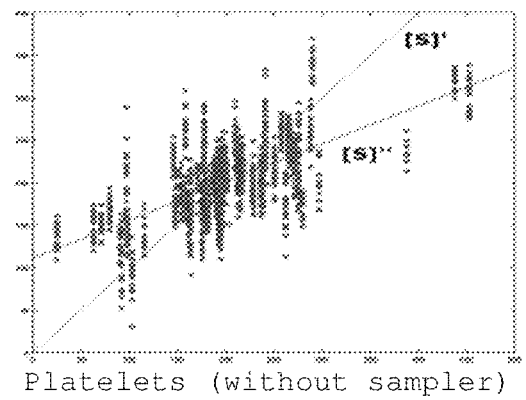
Figure 7A:
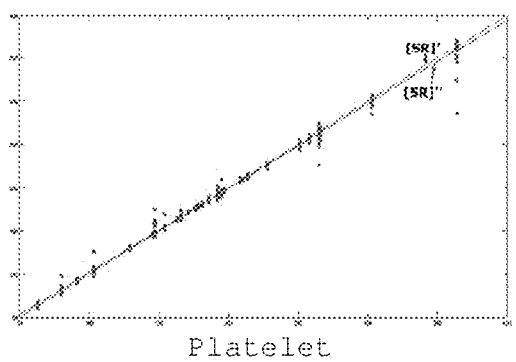
FIGS. 7A to 7H show the final result of the concentration of 8 biomarkers used as an example after an average of 90 iterations to obtain N∥ and after an average of 60 iterations to obtain $\overline{[Z]}$. The axis in these figures refer to the standard obtained from an invasive method [S] against [SR]' and [SR]". This calibrated numerical set $\overline{[Z]}$ is encoded and implemented in a dedicated digital circuit to operate directly, receiving the filtered spectra and encoding them at their respective biomarkers concentrations.
Figure 7B:
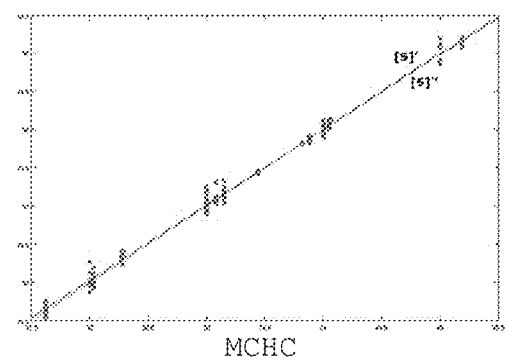
Figure 7C:
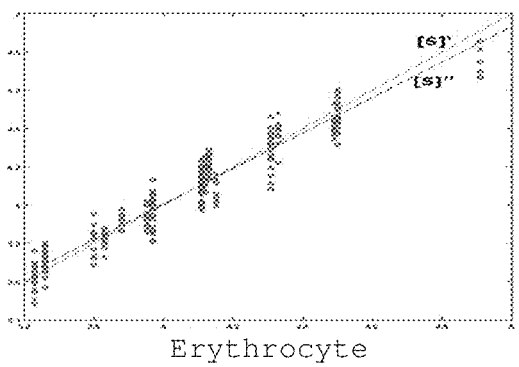
Figure 7D:
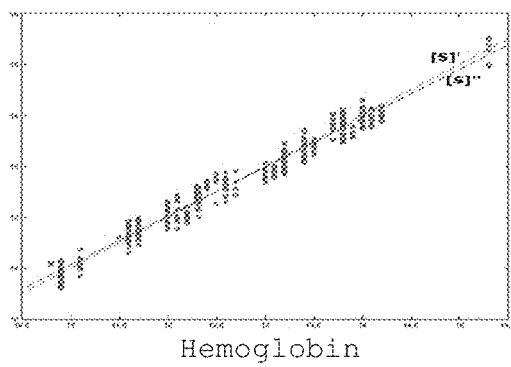
Figure 7E:
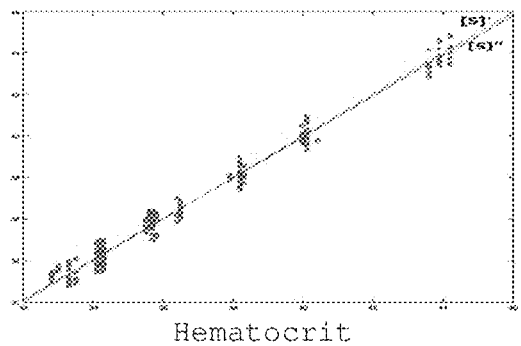
Figure 7F:
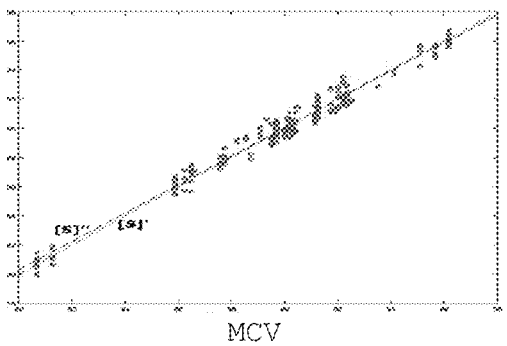
Figure 7G:
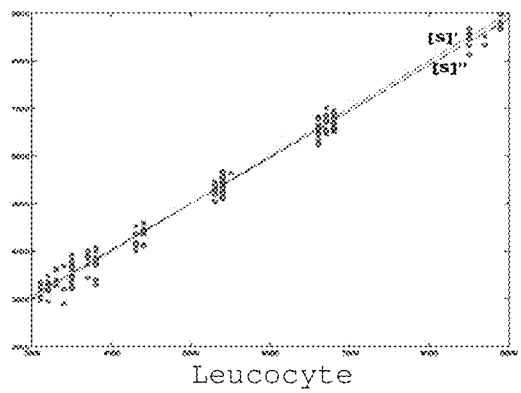
Figure 7H:
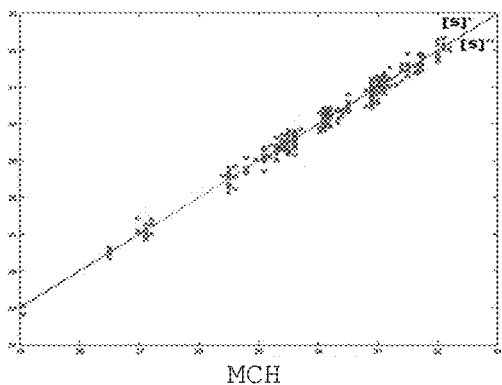

2. Obtaining biochemical data from living tissues and in a non-invasive way also depends on an equipment that has a sampler with an ergonomic shape to fit the fingers of the human hand and the adequate measurements to collect the reflectance detected by the spectrophotometer. FIGS. 6A and 6B show the importance of that geometry.

3. A software annuls the possibility of sample variability, and guarantees the traceability and reliability of the whole process. The software, beyond processing the digital filter-decoder pair N‖-[Z], also organizes and registers all proceedings, surveilles (keeps under surveillance or close observation) and validates the data collection of the samples and proper calibration standards B-W or 2% and 99%. In the calibration of each spectrophotometer, when the B-W spectral curves are received they are compared with those previously stored in this software and if this comparison results in a deviation that is less than 0.001, the sample collection proceeding continues. To collect samples [T], the software collects an average of 1000 spectra in less than 60 seconds. After the average and standard deviation are calculated, the spectra average is accepted as a valid sample if the standard deviation is less than 0.001.

Figure 4:
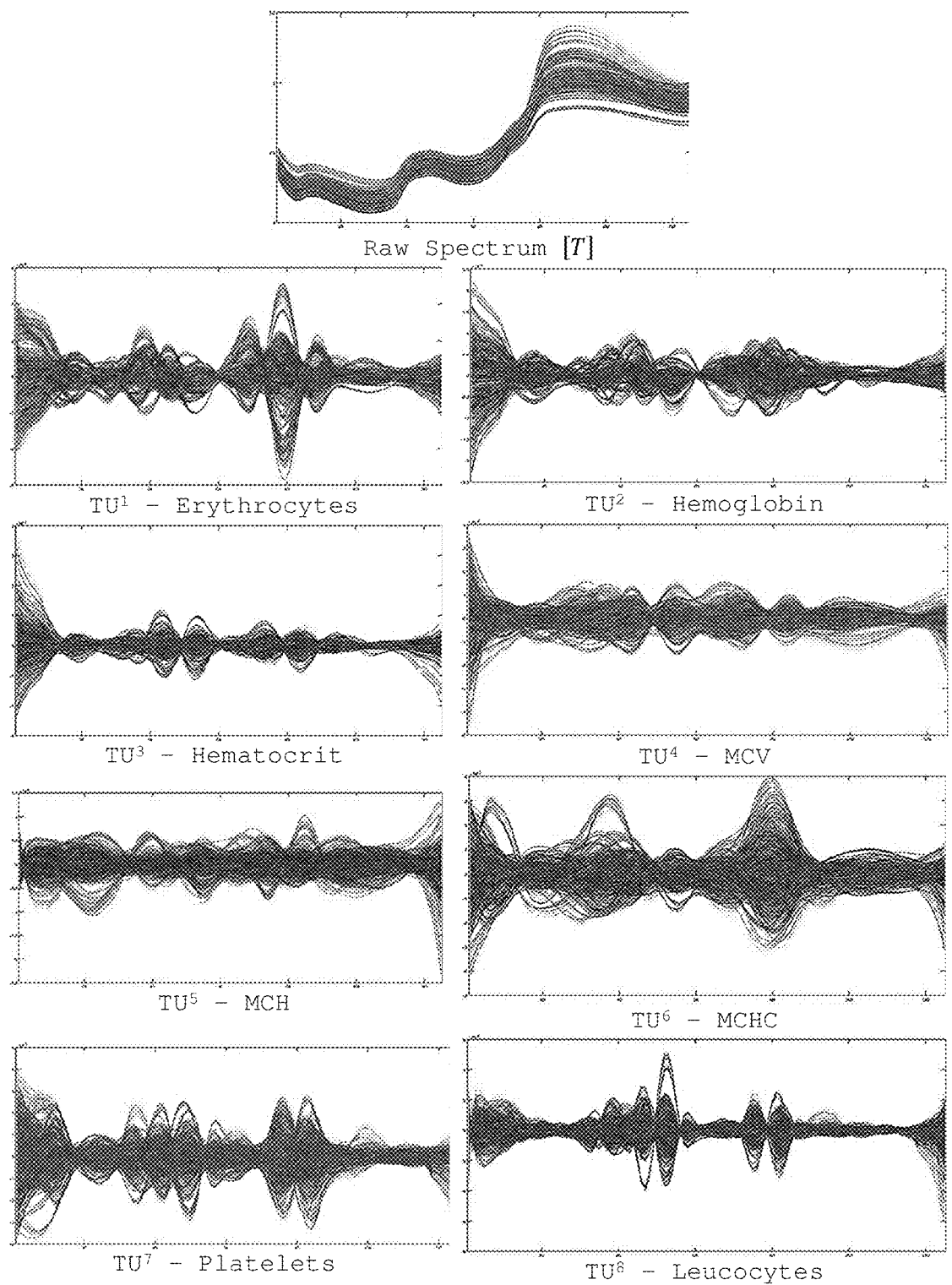
FIG. 4 shows an example, with 8 biomarkers, of the application of filter N∥ where the raw spectrum [T] is decomposed in $[T]^1$, $[T]^2$, ..., $[T]^8$. In this example the order of the iterative process step is irrelevant, it only illustrates the filtration N∥ concept.

4. The digital filtering N‖ process shown in the FIGS. 1, 2C and 4, corresponds to the breaking down of a raw spectrum obtained from living tissue in n sub-spectra correspondent to relevant n biomarkers, which are encoded in the form of a hypercube $[^1[TU]_m{}^k]^{1 \cdots n}$ in such a way that the respective decoding or quantification of n biomarkers can be made simultaneously in the determination step. As an example, FIG. 4 shows the decomposition or the filtration of a raw spectra in eight sub-spectra correspondent to each biomarker, all through dedicated digital circuits, parameterized from a numerical basis $[^1[TU]_m{}^k]^{1 \cdots n}$ constructed by calibration and validation.

5. In the calibration and validation step, the algorithms available in the scientific literature cannot be chosen randomly or by convenience, but need to be a determination of one or a combination between two or more algorithm, and in a specific sequence. Furthermore, each biomarker determines a combination of different algorithms. This fact allows to create the digital filter-decoder pair N‖-[Z], which, after being implemented in a digital circuit, allows obtaining the concentration of n biomarkers simultaneously.

6. Using a portable spectrophotometer in the spectral interval between 400 to 2500 nm without optical components susceptible to movement, and as the results are shown simultaneous and in real time, the equipment referred to in this invention can universalize this clinical analysis tool to be used in remote areas without laboratorial infrastructures, war zones, natural disaster zones, among others.

7. The data grouping related to the pathologies or health conditions [μ] of each individual, optimize the creation of the and efficient digital filter-decoder pair N∥-[$\overline{Z}$] to the set of n biomarkers being analysed. Such grouping, if not performed, might not allow the iterative process to converge to a valid solution, as can be observed by comparing the results shown in FIGS. 5A and 5B.

Figure 2A:
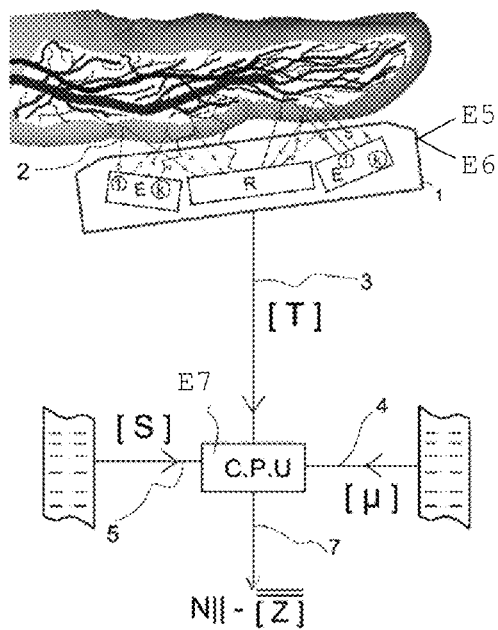
FIG. 2A illustrates the first step of this invention, the calibration and validation step, which is the method to create a digital filter-decoder pair N∥$\overline{[Z]}$ that breaks down the raw spectrum [T] in sub-spectra and decodes them to obtain the concentration of n biomarkers. The calibration and validation have as a reference standard the value of the concentration of biomarkers [S] from the samples obtained in an invasive way and in an conventional way and simultaneously with the spectra [T] collection and the health state [μ]. This figure has a schematic representation of the spectrophotometer (E5) (E6), the analysis area (2), spectra (3), health conditions (4), standard references (5), processing central unit (E7) and the results from the digital filter-decoder pair (7).

To detail the calibration step of this invention, consider the set of data obtained as illustrated in FIG. 2A:

$${}^1[S]_m^{n\ 1}\ [T]_m^{k\ 1}[\mu]_m^{\ j}$$

Where:

[S]→reference or reference standard set of n biomarkers for the calibration and validation, obtained from invasive analysis of m individuals simultaneously obtaining [T] spectra;

[T]→set of k spectral signatures or reflectance emitted by the markers of all living tissues from individuals 1 to m, also named raw spectra. The raw spectra shall be in the interval between 400 to 2500 nm, preferably in the interval between 600 to 1700 nm;

[μ]→set that encodes j clinical pathologies of m individuals;

n→number of biomarkers;

m→number of individuals;

k→number of spectra to each individual [400 ... 2500] nm, of the same group m;

j→amount of pathologies referenced.

FIG. 11 shows an example of the data set ${}^1[S]_m^{n\ 1}[\mu]_m^{\ j}$. A random separation into two groups is performed from this same data:

[S]'[T]'[μ]' which corresponds to approximately ⅔ of the complete set and is the data used in the iterative process of calibration to obtain the digital filter-decoder pair N∥-[$\overline{Z}$];

[S]″[T]″[μ]″ which corresponds to the data complement (approximately ⅓) and is the data used in the validation, which is what qualifies and validates the calibration of the whole process. In the iterative process, in the θ step, applying [T]″ to the digital filter-decoder pair N∥-[$\overline{Z}$] a [SR]″ is obtained which, when compared with the standard reference [S]″, assesses the error obtained for each n biomarker, qualifying and validating the process.

This data separation is possible because the speed and amount of samples with standard deviation less than 0.001 allows considering the set as homogeneous.

The use of pathological data [μ]' of each individual, applied to the n biomarkers [S]', results in:

$$[SU]=[S]'\oplus[\mu]' \quad (1)$$

where [SU] is the grouping of biomarkers [S]', according to the pathologies registered in [μ]', for example:

| Individual | Gly-caemia [S] | Diabetes [μ] | | Individual | Gly-caemia [S] | Diabetes [μ] |
|---|---|---|---|---|---|---|
| 1 | 90 | 0 | | 1 | 90 | 0 |
| 2 | 180 | 1 | ⇒⊕⇒ | 4 | 85 | 0 |
| 3 | 110 | 1 | | 2 | 180 | 1 |
| 4 | 85 | 0 | | 3 | 110 | 1 |

Figure 5A:
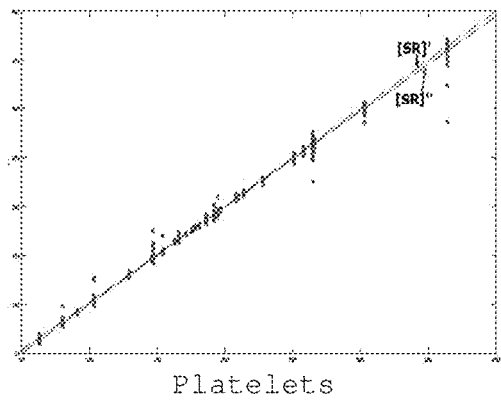
FIGS. 5A and 5B show the comparison between the validation test of [SR]'−[S]'≥[e1] with the application of grouping [SU]'−[S]'⊕[μ]' in the θ iteration, and this same validation test without grouping by pathology and in the same iteration θ. This grouping represents a better performance in the process, and the final result has more precision. The axis in these figures refer to the standard obtained from an invasive method [S] against [SR]' and [SR]".
Figure 5B:
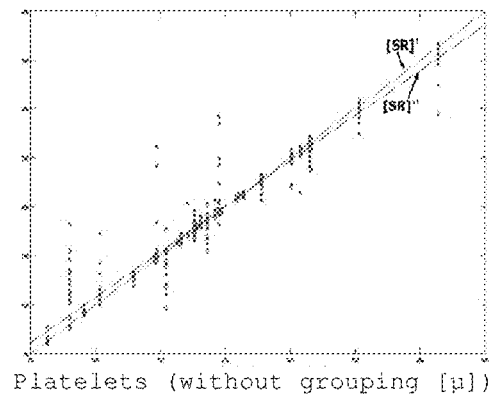

The digital filter-decoder pair N∥-[$\overline{Z}$], obtained when this ordering is performed, is about 20% more efficient when compared with the same amount of iterations without the ordination, as can be seen in the example of FIGS. 5A and 5B.

In the same way:

$$[TU]=[T]'\oplus[\mu]' \quad (2)$$

After the conclusion of the separation and ordering of data, the next step is an iterative process.

The aim of the first step in the iterative process named "pre-processing" or "numerical filtering" (illustrated in FIGS. 1, 2C and 4), is to parametrize a digital filter to break down the raw spectra into sub-spectra correspondent to each biomarker, in the following way:

$$[TU]^N=N\|[TU] \quad (3)$$

Where:

$$N\|\begin{cases} 1^a P_1 = \text{Centering in the average} \\ 2^a P_2 = \text{Applying the first derivative} \\ 3^a P_3 = \text{Normalization by the square minimums} \\ \ldots \\ i^a P_i = P_1 \cup P_2 \\ \ldots \\ k^a P_k = P_n \cup P_1 \cup P_3 \\ n^a P_n = P_1 \cup P_i \cup P_1 \cup \ldots P_n \end{cases}$$

Being:

$P_n$→the set of n mathematical operators, including but not limited to those referenced in FIG. 12;

N→number of biomarkers (1 to n), meaning that a hypercube of dimensions 1 to k columns, 1 to m lines and 1 to N levels $[{}^1[TU]_m^{k}]^{1\ \cdots\ N}$ is created.

Each level of the hypercube $[TU]^N$ is created with a specific sequence of $P_n$ and or a specific combination between different $P_n$, correspondent to each type of biomarker.

The order, the sequence and the combination of each operator $P_n$ to be applied to the matrix [TU] spectra is determinant on the calibration of each biomarker and consequently, of the digital filter-decoder pair N∥-[$\overline{Z}$], because it is through the sequence and the combinations of $P_n$ that the interferences caused by different tissues can be filtered so the spectra of the markers in human blood and their respective biomarkers stand out. FIG. 4 shows an example of eight sub-spectra obtained with a N∥ filter. FIG. 15 summarizes the application of $P_n$ properly ordered, applied to each type of biomarker.

After performing the steps of ordering and applying the filter N∥ to obtain $[{}^1[TU]_m^{k}]^{1\ \cdots\ N}$, the hyperplanes are constructed:

$$[\overline{Z^1}]=[\overline{su^1}]'\Theta[\overline{TU}]^1;\ [\overline{Z^2}]=[\overline{su^2}]'\Theta[\overline{TU}]^2;\ \ldots;$$
$$[\overline{Z^N}]=[\overline{su^N}]'\Theta[\overline{TU}]^N \quad (4)$$

Where:

[$\overline{Z^1}$]→hyperplane of z levels of the i biomarker and with dimension 1 to k (spectrum), as can be seen in FIGS. 13A and 13B. The z levels vary according the algorithm used;

[$\overline{su^i}$]'→vector of 1 to m dimension which contains the concentration of biomarker i of m individuals;

$[\overline{TU}]^i$→plane i of the hypercube $[\overline{TU}]^N$ with the spectra 1 to k correspondent to biomarker i of m individuals.

For the operator Θ of the same form as N∥, the choice, including but not restricted to, of the algorithms referred to in FIG. 12 is determinant on the construction of the decoder [$\overline{Z}$]. This choice depends on the type of biomarker being analysed.

The hypercube is then constructed:

$$[\overline{Z}]=[\overline{Z^1}]\oplus[\overline{Z^2}]\oplus\ldots\oplus[\overline{Z^N}] \quad (5)$$

where the operator ⊕ unites the hyperplanes [$\overline{Z^N}$] obtained by equation (4).

FIGS. 13A and 13B show two distinct planes of the hypercube $\overline{[Z]}$ correspondent to eight different biomarkers used as an example.

The numbers that make this hypercube are named latent variables and are the result of the numerical processing of the algorithms used for each $\Theta$, highlighted in the composition spectrum of the respective biomarker. Each hyperplane $[\overline{Z^i}]$ can be built with different z levels depending on the biomarker and the kind of algorithm used to highlight these latent variables (or biomarker composition identifiers). This happens in a way that the hypercube $\overline{[Z]}$, obtained by equation (5), considers the hyperplane $[\overline{Z^i}]$ with the highest z level and the empty spaces of the other hyperplanes are filled with zeros, maintaining the cubic structure of the decoder $[\overline{Z^i}]$ independent of the $\Theta$ used.

Figure 1:
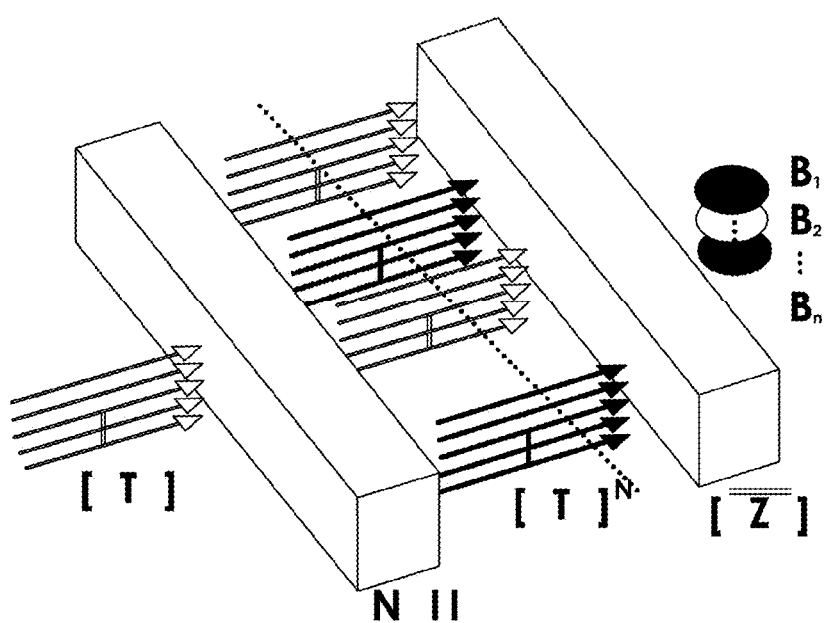
FIG. 1 shows the basic structure of this invention, which in real time and simultaneously, obtains a raw spectrum [T] that contains the digital signatures of the living tissue of an individual, filters N∥ and obtains the $[T]^N$ spectra that matches each [S] biomarker of human blood and decodes them $\overline{[Z]}$ in the concentration of the relevant biomarkers $B_1$, $B_2$, ..., $B_n$.
Figure 2B:
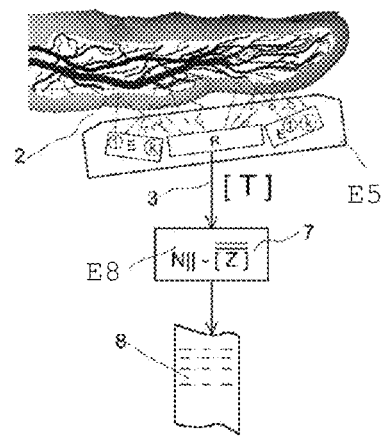
FIG. 2B illustrates the second step of this invention, the determination step or routine work, which is performed only after the calibration and validation step is finished. In this process the concentration of biomarkers are obtained in real time and simultaneously. This figure shows the schematic representation of a spectrophotometer (E5), the analysis area (2), the reflectance spectra (3), the processing central unit (E8) with the digital filter-decoder pair (7), and the result of the set of biomarkers (8).
Figure 2C:
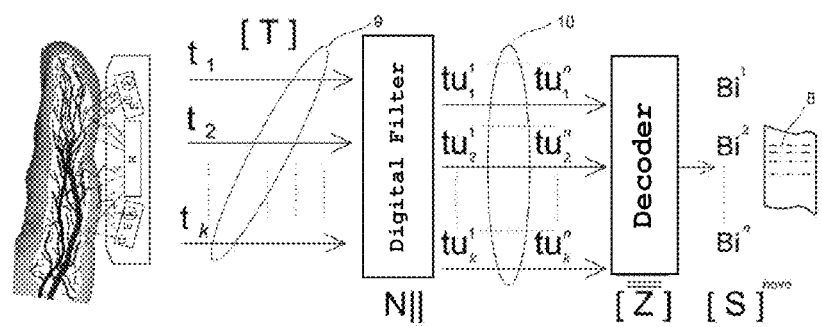
FIG. 2C shows the method to obtain and process the concentration of biomarkers. The filter N∥ is applied to spectrum [T] of living tissue from an individual, to obtain sub-spectra $[T]^N$ that corresponds to each relevant biomarker. The sub-spectra are decoded in $\overline{[Z]}$ afterwards to obtain the simultaneous concentration of these relevant biomarkers in real time. This figure shows a schematic representation of the result for the set of biomarkers (8), the reflectance spectra in the determination step (9), and the spectra processed by the digital filter-decoder pair (10).

$\overline{[Z]}$ is named digital decoder, as shown in FIGS. 1 and 2C. This decoder, in the determination step, transforms the spectral data into concentration of biomarkers data, in the same format of the samples [S] obtained in an invasive way, simultaneously and in real time.

The first set of numerical values for n biomarkers, named [SR]' in this stage of the iterative process, is obtained by:

$$[SR]' = \overline{[Z]} * [TU]^{N'} \quad (6)$$

and equation (7) details equation (6) in the operation that obtains this first set of values correspondent to the concentration of n biomarkers:

$$\begin{bmatrix} b_1^{1'} & \cdots & b_1^{n'} \\ \vdots & \ddots & \vdots \\ b_m^{1'} & \cdots & b_m^{n'} \end{bmatrix} = \begin{bmatrix} z_1^1 & \cdots & z_1^n \\ \vdots & \ddots & \vdots \\ z_k^1 & \cdots & z_k^n \end{bmatrix}^{1 \cdots z} * \begin{bmatrix} tu_1^1 & \cdots & tu_k^1 \\ \vdots & \ddots & \vdots \\ tu_1^m & \cdots & tu_k^m \end{bmatrix}^{1 \cdots N'} \quad (7)$$

where:
N, n→number of biomarkers;
m→number of individuals;
k→number of spectra;
z→amount of levels of the highest hyperplane of $[\overline{Z^i}]$ obtained by $\Theta$;
*→performs the algebraic operations of matrix multiplication between each hyperplane of the hypercube $\overline{[Z]}$ and each plane of the hypercube $[^1[TU]_m^k]^{1 \cdots N}$ to obtain the matrix [SR]' of these n biomarkers.

At this point in the iterative process, the actual digital filter-decoder pair $N\|-\overline{[Z]}$ is qualified. Be a matrix [e1] containing the maximum errors allowed (<than 1%) between the standard reference biomarkers [S]', and those obtained in this step, or being:

If $|[SR]'-[S]'| \geq [e1]$, then it returns to the numerical filtering $N\|$ process with the re-ordering, and/or addition and/or exclusion of numerical operators belonging to the $P_n$ set, otherwise the original data $[S]"[T]"[\mu]"$ is used to obtain:

$$[SR]" = \overline{[Z]} * [TU]^{N"} \quad (8)$$

and in this way, be a matrix [e2] containing the maximum errors allowed (<than 1%) between standard reference biomarkers [S]" and those obtained in this step with the aim to validate the process, or being:

If $|[SR]"-[S]"| \geq [e2]$ it returns to the $\Theta$ process with the re-ordering, and/or addition and/or exclusion of known algorithms, otherwise the digital filter-decoder pair $N\|-\overline{[Z]}$ is determined and validated, in such a way that:

$$[S]^{novo} = \overline{[Z]} * [T]^{N^{novo}} \quad (9)$$

or, $$\begin{bmatrix} b_1 \\ \vdots \\ b_n \end{bmatrix}^{novo} = \begin{bmatrix} z_1^1 & \cdots & z_1^n \\ \vdots & \ddots & \vdots \\ z_k^1 & \cdots & z_k^n \end{bmatrix}^{1 \cdots z} * [t_1 \ \cdots \ t_k]^{1 \cdots N^{novo}} \quad (10)$$

These numerical data are then digitized and programmed into a dedicated digital circuit to operate in the determination step, applying the spectrum [T] of a single individual to the filter $N\|$ obtaining the plane $[t_1 \ldots t_k]^{1 \cdots N^{novo}}$ and its biomarker concentration $b_1$ to $b_n$, according to equation (10), all in real time and simultaneously.

FIG. 15 shows the biomarkers used, with the respective algorithms referred to in FIG. 12, the amount of samples necessary to obtain the convergence and the amount of corresponding iterations. The biomarkers analysed are not limited to those referred in FIG. 15, others can also be considered.

DESCRIPTION OF A PREFERRED EMBODIMENT

FIG. 2A shows the schematic operation of the calibration and validation method for the digital filter-decoder pair $N\|-\overline{[Z]}$. In this step the spectra [T] of 1 to m individuals, the pathologies [$\mu$] of those same individuals, and the n biomarkers [S] obtained from conventional and invasive methods, are collected simultaneously and sent to the processing system to construct the digital filter-decoder pair $N\|-\overline{[Z]}$, that will later be used in the determination step, via a dedicated digital circuit.

Figure 3:
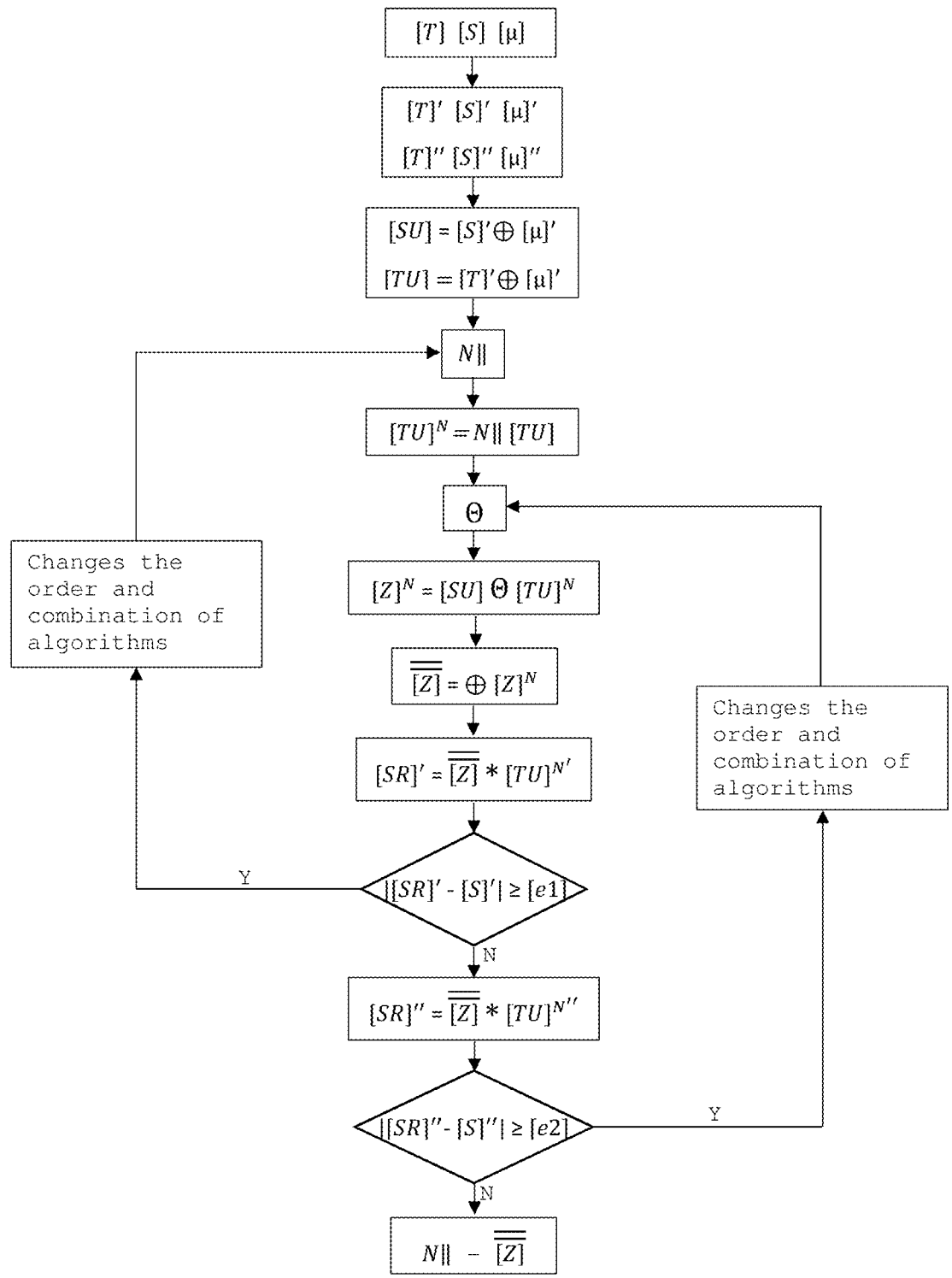
FIG. 3 shows the algorithm used in the calibration and validation step to manipulate the samples, the creating of filter N∥ and decoder $\overline{[Z]}$ in an iterative process until the validation guarantees that for each new spectrum [T] a new set of valid concentration of biomarkers [S] is obtained.

FIG. 3 shows the algorithm used in the method of calibration and validation step that allows to calibrate and validate the digital filter-decoder pair $N\|-\overline{[Z]}$ as mentioned above.

The equipment described by FIG. 9 uses a software to:
Organize the collection of spectra and guarantee its reliability (without variability);
Optimize the data register of standard references of biomarkers [S] obtained in an invasive way;
Organize the register of patient identification, its health condition [$\mu$], and generate a traceable data base to be used in the algorithm to create the digital filter-decoder pair $N\|-\overline{[Z]}$.

The equipment referred to in the present invention can be installed in different locations that collect material for conventional and invasive clinical analysis. The spectra [T] of the finger of a patient can also be collected simultaneously with the collection of blood with syringes from the same patient. Each patient is interviewed to collect complementary data, such as the health conditions and possible pathologies. The process is registered to guarantee the traceability of the act through a software that registers the identity of the patient and the ID of the conventional invasive collection. All is registered in a single data base $^1[S]_m^{n\ 1}\ ^{[T]}_m^{k\ 1[\mu]}_m^{j}$.

To each spectra [T] the spectrophotometer is calibrated in its "Black" and "White" or B-W references, (standards 2% and 99% respectively). The software installed in the equipment has a valid registry of the spectral curves of these two standard references B-W. When the B-W spectral curves are received, they are compared and stored in the software. This way the spectrophotometer calibration is not only performed but the calibration is also verified.

A possible variability of the spectral samples $^1[T]_m^k$, especially because they are living tissue, is annulled since the equipment is prepared to collect an average of a thousand spectra in less than sixty seconds and, after the average and standard deviation are calculated, the average of the spectra is accepted as a valid sample if the standard deviation is less than 0.001. Also, this collection speed (15 samples per second), corresponds to an instantaneous of the blood components, which in itself would be sufficient to minimize questions of living tissue variability, mainly because of the blood flux and possible movement of the collection region: the finger of the patient. However, if such precision is not achieved, the sampler (E1) and the finger of the patient are cleaned. If the problem still remains after three consecutive times without precision, the system is interrupted and substituted, to always guarantee the precision and reliability in the data obtained.

Nevertheless, the fact that samples [S] from conventional invasive methods might have some kind of problem, due to an incorrect collection, or due to the conventional chemical and laboratorial kits, cannot be excluded. This is taken into consideration and the data that is outside the region chosen as standard is discarded from [S], [T] e [μ].

The data set $^1[S]_m^{n\ 1\ [T]}{}_m^{k\ 1[\mu]}{}_m^{j}$ is considered sufficient to the process of creating the digital filter-decoder pair N||-[Z] when the total valid samples are higher than two hundred for each biomarker. The term "valid samples" refers to those whose average has a standard deviation that is less than 0.001, in a universe of a thousand simultaneous samples.

When the set of valid samples is obtained, the algorithm of the method referred to in FIG. 3 is implemented. The process is performed in a data processing room and, for each biomarker the creation of the digital filter-decoder pair N||-[Z] can take up to thirty hours.

When the first step is finished, and before starting the determination step, each new spectrophotometer used in the second step, is gauged by comparison. This gauging or calibration transfer process is performed, for example but not limited to, to the standards 99%, 80%, 60%, 40%, 20%, 10%, 5%, and 2% (including but not limited to: Middleton Spectral Vision MRC-910-LIN8, Serial Number 0106, Calibration #AT-20080917-1), in a way that the parameters of the digital filter-decoder pair can be transferred in scale and be traceable.

The determination step uses the same kind of equipment used in the calibration and validation step, and the same management software which guarantees the quality and traceability of the set [T] and [μ] of each individual, as described next. In this step, the spectra [T] are also processed in the digital filter-decoder pair N||-[Z], and the concentrations of biomarkers are shown afterwards, simultaneously and in real time.

In this determination step, the spectrophotometer is periodically gauged by two standard references B-W, including but not limited to: 2% e 99% (MRC-910-LIN8, Serial Number 0106, Calibration #AT-20080917-1). If the result of these operations is not acceptable, the operations previously described are implemented, to guarantee the reliability of samples and results.

FIGS. 2B and 2C show the process in the determination step, where each sample [T] consists in an average of a thousand spectra collected in less than sixty seconds. After the average and standard deviation are calculated, the average of the spectra is accepted as a valid sample if the standard deviation is less than 0.001. Similarly to the proceeding in the first step, if a deviation occurs the window of the sampler and the finger of the patient is cleaned. If the precision is still below the value regarded as standard, the equipment is substituted, guaranteeing the quality of the proceeding.

In the processing central unit and in real time (less than 5 minutes), each sample [T] collected is qualified by the standard deviation, filtered and decoded by the digital filter-decoder pair N||-[Z], and the concentration of the correspondent set of biomarkers is generated simultaneously.

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by applicants, pursuant to 37 C.F.R. 01.57 (b) (1), to relate to each and every individual publication, database entry (e.g., Genbank sequences or GeneID entries), patent application, or patent, each of which is clearly identified in compliance with 37 C.F.R. 01.57 (b) (2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Those skilled in the art will recognize, or be able to ascertain using no more than routine experimentation, many equivalents to the specific embodiments of the invention described herein. Such equivalents are intended to be encompassed by the following claims.

Bibliography

Furukawa Hiromitsu, "Real-time multi-channel Fourier transform spectroscopy and its application to non-invasive blood fat measurement", Sensing and Bio-Sensing Research, Elsevier, March 2016.

Sakudo A., "Near-infrared spectroscopy for medical applications: Current status and future perspectives", Clinica Chimica Acta 455 (2016) 181-188.

M. Isabel López, M. Pilar Callao, Itziar Ruisánchez, "A tutorial on the validation of qualitative methods: From the univariate to the multivariate approach", Elsevier, Analytica Chimica Acta 891 (2015).

Frank Westad, Federico Marini, "Validation of chemometric models—A tutorial", Elsevier, Alalytica Chimica Acta 893 (2015).

Schmitz S. K., Hasselbach P. P., Ebisch B., Klein A., Pipa G., Galuske R. A. W., "Application of Parallel Factor Analysis (PARAFAC) to electrophysiological data", Frontiers in Neuroinformatics, 30 Jan. 2015.

Yoshida S. et al., "Optical screening of diabetes mellitus using noninvasive Fourier transform infrared spectroscopy technique for human lip", Journal of Pharmaceutical and Biomedical Analysis, vol. 76, pp. 169 to 176, 2013.

Portugal Cohen M. et al., "Non-invasive evaluation of skin cytokines secretion: An innovative complementary method for monitoring skin disorders", Methods 61 (2013) 63-68.

Sakudo A. et al., "Analysis of Vis-NIR spectra changes to measure the inflammatory response in the nasal mucosal region of influenza A and B virus-infected patients", Journal of Clinical Virology 55 (2012) 334-338.

Hideyuki S., Masakazu N., Toshiyuki T., Kenzi S., Wataru K., "PARAFAC Analysis for Temperature Dependent NMR Spectra of Poly (Lactic Acid) Nanocomposite", Chemometrics in Practical Applications, Cap. 13, 2012.

Portugal Cohen M. et al., "Noninvasive skin biomarkers quantification of psoriasis and atopic dermatitis: Cytokines, antioxidants and psoriatic skin autofluorescence", Biomedicine & Pharmacotherapy, vol. 66, pp. 293 to 299, 2012.

Sakudo A. et al., "Visible and near-infrared spectra collected from the thumbs of patients with chronic fatigue syndrome for diagnosis", Clinica Chimica Acta, vol. 413, pp. 1629 to 1632, 2012.

Katheem M. Farhan, Thottapalli P. Sastry, Asit B. Mandal, "Comparative study on secondary structural changes in diabetic and non-diabetic human finger nail specimen by using FTIR spectra", Clinica Chimica Acta 412 (2011) 386-389.

Portugal Cohen M. et al., "Noninvasive skin measurements to monitor chronic renal failure pathogenesis", Biomedicine & Pharmacotherapy 65 (2011) 280-285.

Carlos F. Amaral *, Martin Brischwein, BernhardWolf, "Multiparameter techniques for non-invasive measurement of blood glucose", Sensors and Actuators B 140 (2009) 12-16.

Sidiropoulos N. D., "Adaptive Algorithms to Track the PARAFAC Decomposition of a Third Order Tensor", IEEE Transactions On Signal Processing, vol. 57, No. 6, June 2009.

Rosipal R., Trejo L. J. and Nunez P. L., "Application of Multiway EEG Decomposition for Cognitive Workload Monitoring", Part 2 Application Research, 2009.

Sakudo A. et al., "Noninvasive prediction of hematocrit levels by portable visible and near-infrared spectrophotometer", Clinica Chimica Acta, vol. 408, pp. 123 to 127, 2009.

Kobayashi, T., et al, "Portable visible and near-infrared spectrophotometer for triglyceride measurements", International Journal of Molecular Medicine, 23: 75-79, 2009.

F. Marini, R. Bucci, A. L. Magri, A, D. Margri, "Artificial neural networks in chemometrics: History, examples and perspectives", Elsevier, Microchemical Journal 88 (2008).

Amaral Carlos E, F., "Multiparameter Methods for Noninvasive Measurement of Blood Glucose", Doktors Ingenieurs, Munich, January 2008.

McMurdy J. W., Gregory D. J., Suner S., Crawford G., "Noninvasive Optical, Electrical and Acoustic Methods of Total Hemoglobin Determination", Clinical Chemistry, vol. 54:2, pp. 264 to 272, 2008.

Kroonenberg P. M., "Applied Multiway Data Analysis", John Wiley & Sons, Inc., Hoboken, N.J., 2008.

Bo-Yan Li, "Comparison of performance of partial least squares regression, secured principal component regression, and modified secured principal component regression for determination of human serum albumin, γ-globulin and glucose in buffer solutions and in vivo blood glucose quantification by near-infrared spectroscopy", Anal Bioanal Chem (2007) 387:603-611.

Sakudo A. et al., "Nearinfrared spectroscopy: Promising diagnostic tool for viral infections", Biochemical and Biophysical Research Communications, vol. 341, pp. 279 to 284, 2006.

Muhammad A. Razi, Kuriakose Athappilly, "A comparative predictive analysis of neural networks (Nns), nonlinear regression and classification and regression tree (CART) models", Elsevier, Expert Systems with Applications 29 (2005).

Riccardo Leardi, "Nature-Inspired Methods in Chemometrics: Genetic Algorithms and Artificial Neural Networks", Elsevier, Data Handling in Science and Technology, Vol. 23, December 2003.

Philip K. Hopke, "The evolution of chemometrics", Elsevier, Analytica Chimica Acta 500 (2003).

Geladi P. et al., "Three-way modeling of a batch organic synthesis process monitored by near infrared spectroscopy" Journal of Near Infrared Spectroscopy, vol. 9, pp. 1 to 9, 2001.

Gurden S. P., Westerhuis J. A., Bro R., Smilde, A. K., "A comparison of multi-way regression and scaling methods", Chemometrics and Intelligent Laboratory Systems, vol. 59, pp. 121 to 136, 2001.

Wold S. et al., "PLS regression: a basic tool of chemometrics". Chemometrics and Intelligent Laboratory Systems, vol. 58:2, pp. 109 to 130, 2001.

Anderson C. et al., "Special Issue: Multiway Analysis" Journal of Chemometrics Eds., vol. 14, 2000.

Anderson C. A., Bro R., "The n-way Toolbox for MATLAB", Chemometrics and Intelligent Laboratory Systems, vol. 52, pp. 1 to 4, 2000.

Xiaomao Wu, Shu-jen Yeh, Tzyy-Wen Jeng, and Omar S. Khalil, "Noninvasive Determination of Hemoglobin and Hematocrit Using a Temperature-Controlled Localized Reflectance Tissue Photometer", Analytical Biochemistry, vol. 287, pp. 284 to 293 (2000).

Frédéric Despagne and D. Luc Massart, "Neural networks in multivariate calibration", The Analyst, August 1998.

Bro R., "Multiway analysis in the food industry: models, algorithms, and applications" Ph. D. Thesis, Royal Veterinary and Agricultural University, Denmark, 1998.

Bro R., "PARAFAC—Tutorial and applications", Chemometrics and Intelligent Laboratory Systems, vol. 38, pp. 149 to 171, 1997.

Bro R., "Multiway calibration. Multilinear PLS", Journal of Chemometrics, vol. 10, pp. 47 to 63, 1996.

Smilde A., "Three-way analyses. Problems and prospects", Chemometrics Intelligent Laboratory Systems, vol. 14, pp. 143 to 157, 1992.

Geladi P., "Analysis of multiway (multimode) data" 29 Chemometrics Intelligent Laboratory Systems, vol. 7, pp. 11 to 30, 1989.

Kiers H. A. L., "Three-way methods for the analysis of qualitative and quantitative two way data", DSWO Press, University of Leiden, 1989.

Marten, H. N. T., "Multivariate Calibration", New York: Wiley, 1989.

Kroonenberg P. M., "Three-mode Principal Component Analysis", 1983 DSWO Press, Leiden, Reprint 1989.

Wold S. et al., "Principal component analysis" Chemometrics Intelligent Laboratory Systems, vol. 2, pp. 37 to 52, 1987.

Kroonenberg P. M., Leeuw J., "Principal Component Analysis Of ThreeMode Data By Means Of Alternating Least Squares Algorithms", Psychometrika, vol. 45, No. 1. March, 1980.

Harshman R. A., "Foundations of the Parafac procedure: Model and conditions for an explanatory multimode factor analysis" UCLA Working Papers in Phonetics, vol. 16, pp. 1 to 84, 1970.

Carrol J. D., "Analysis of individual differences in multidimensional scaling via an m-way generalization of the EckartYoung decomposition" PSYCOMETRIKA, vol. 35, pp. 282 to 319, 1970.

The invention claimed is:

1. A sampler (E1) for simultaneously determining in real time a non-invasive concentration of several biomarkers, the sampler (E1) comprising:
   a first substantially ellipsoidal shape (c1) and a second substantially ellipsoidal shape (c2) that have axis with different lengths, and which are substantially centered and parallel to each other,
   wherein the first substantially ellipsoidal shape (c1) comprises:
      an $x_1$ axis with a length between 0.01 mm and 40 mm,
      a $y_1$ axis with a length between 0.01 mm and 45 mm, and
      a height $d_1$ between 0.01 mm and 18 mm
   that is found immediately above the second substantially ellipsoidal shape (c2) wherein the second substantially ellipsoidal shape (c2) comprises:
      an $x_2$ axis with a length between 0.01 mm and 31 mm,
      a $y_2$ axis with a length between 0.01 mm and 36 mm, and
      a height $d_2$ between 0.01 mm and 29 mm
   with an inferior surface of the first substantially ellipsoidal shape (c1) showing a substantially convex shape that unites a superior edge of the first substantially ellipsoidal shape (c1) and the edge of the second substantially ellipsoidal shape (c2).

2. The sampler (E1) of claim 1, wherein the sampler (E1) is made of a polymeric based material.

3. The sampler (E1) of claim 2, wherein the polymeric based material is polytetrafluoroethylene (PTFE).

4. The sampler (E1) of claim 1, wherein the length of the $x_1$ axis is between 10 mm and 30 mm.

5. The sampler (E1) of claim 1, wherein the length of the $x_1$ axis is between 18 mm and 20 mm.

6. The sampler (E1) of claim 1, wherein the length of the $y_1$ axis is between 10 mm and 35 mm.

7. The sampler (E1) of claim 1, wherein the length of the $y_1$ axis is between 23 mm and 26 mm.

8. The sampler (E1) of claim 1, wherein the height of $d_1$ is between 1 mm and 13 mm.

9. The sampler (E1) of claim 1, wherein the height of $d_1$ is between 3 mm and 8 mm.

10. The sampler (E1) of claim 1, wherein the length of the $x_2$ axis is between 5 mm and 21 mm.

11. The sampler (E1) of claim 1, wherein the length of the $x_2$ axis is between 9 mm and 11 mm.

12. The sampler (E1) of claim 1, wherein the length of the $y_2$ axis is between 10 mm and 26 mm.

13. The sampler (E1) of claim 1, wherein the length of the $y_2$ axis is between 14 mm and 16 mm.

14. The sampler (E1) of claim 1, wherein the height of $d_2$ is between 1 mm and 19 mm.

15. The sampler (E1) of claim 1, wherein the height of $d_2$ is between 2 mm and 9 mm.

16. A method of parameterizing digital circuits and non-invasively determining the concentration of several biomarkers simultaneously and in real time with the sampler (E1) of claim 1, the method comprising:
   a calibration step and a validation step, wherein the calibration and the validation steps comprise:
      a) obtaining a concentration of biomarkers [S], health conditions, and pathologies [μ] of a group of subjects obtained in an invasive and conventional way,
      b) obtaining, from the same group of subjects, with the sampler (E1), [T] spectra in a near infrared range from 400 to 2500 nm,
      c) separating each sample, the sample being obtained in an invasive and conventional way and the sample being obtained from the spectra, in sets of ⅔ [S]'[T] '[μ]' and ⅓ [S]"[T]"[μ]" of a total data to obtain a digital filter-decoder pair N∥-[Z],
      d) grouping the samples by pathology,
      e) applying combinations of mathematical algorithms to the groups of subjects to obtain the filter N∥ and the decoder [Z],
      f) validating the digital filter-decoder pair N∥-[Z] with maximum errors allowed of <than 1% between ⅔ of the standard reference biomarkers [S]' and ⅔ of the biomarkers obtained from the filtered and decoded spectra, through an intermediate validation test of the digital filter-decoder pair N∥-[Z],
      g) returning to step e) if the validation in step f) is negative,
      h) validating the digital filter-decoder pair N∥-[Z] with the maximum errors allowed of <than 1% between ⅓ of the standard reference biomarkers [S]' and ⅓ of the biomarkers obtained from the filtered and decoded spectra, through the intermediate validation test of the digital filter-decoder pair N∥-[Z];
      i) returning to step e) if the validation in step h) is negative,
      j) obtaining the digital filter-decoder pair N∥-[Z]; and
   a determination step, wherein the determination step comprises:
      a) obtaining, using the sampler (E1), spectral signatures by means of a spectrophotometer,
      b) applying the digital filter-decoder pair N∥-[Z] parameterized in the calibration step, and
      c) obtaining the concentration of biomarkers simultaneously and in real time.

17. The method of claim 16, wherein the spectra analyzed is a reflectance spectra.

18. The method of claim 16, wherein the digital filter N∥ breaks down raw spectra and the digital decoder [Z] obtains the concentration of the biomarkers.

19. The method of claim 16, wherein a data base and the digital filter-decoder pair N∥-[Z] obtained in the calibration and validation steps is used in the determination step in several spectrophotometers.

20. The method of claim 16, wherein the near infrared range is from 600 to 1700 nm.

* * * * *